United States Patent [19]
Baba et al.

[11] Patent Number: 6,036,653
[45] Date of Patent: Mar. 14, 2000

[54] PULSIMETER

[75] Inventors: Norimitsu Baba; Michio Kobayashi; Tsukasa Kosuda, all of Suwa, Japan

[73] Assignee: Seiko Epson Corporation, Tokyo, Japan

[21] Appl. No.: 08/964,966

[22] Filed: Nov. 5, 1997

[30] Foreign Application Priority Data

Nov. 7, 1996 [JP] Japan ................................. 8-295481

[51] Int. Cl.[7] .................................................. A61B 5/02
[52] U.S. Cl. ........................................... 600/500; 600/502
[58] Field of Search .................................. 600/500, 501, 600/502, 503, 518, 481, 490

[56] References Cited

U.S. PATENT DOCUMENTS

| | | | |
|---|---|---|---|
| 5,439,483 | 8/1995 | Duong-Van | 600/518 |
| 5,471,991 | 12/1995 | Shinnar | 600/518 |
| 5,697,374 | 12/1997 | Odagiri et al. | 600/500 |
| 5,749,366 | 5/1998 | Odagiri et al. | 600/502 |
| 5,776,070 | 7/1998 | Kitazawa et al. | 600/503 |

FOREIGN PATENT DOCUMENTS 7-227383  8/1995  Japan .

OTHER PUBLICATIONS

Nature vol. 383, Sep. 26, 1996, pp. 323–327; Scaling behaviour of heartbeat intervals obtained by wavelet–based time–seires analysis; Plamen Ch. Ivanou, et al.; A mechanism for halogen release from sea–salt aerosol in the remote marine boundary layer, Rainer Vogt, et al.

*Primary Examiner*—Cary O'Connor
*Assistant Examiner*—Navin Natnithithadha
*Attorney, Agent, or Firm*—Eric B. Janofsky

[57] ABSTRACT

A pulsimeter analyzes a pulse wave signal output by a pulse wave sensor worn on a part of the body while exercising, enables extraction of only the pulse wave component without being affected by movement of the body, and evaluates a detection state indicative of whether the pulse wave sensor is detecting the pulse. A pulse wave component extractor extracts a pulse wave component from the result of a time-frequency analysis of a pulse wave signal. A pulse rate calculator calculates the pulse rate per minute based on the pulse wave component extracted by the pulse wave component extractor. The pulse rate is then displayed. A detection state of the pulse wave sensor is also displayed by providing a detection state evaluator for determining the presence of a pulse wave component based on the result output by the pulse wave component extractor.

21 Claims, 16 Drawing Sheets

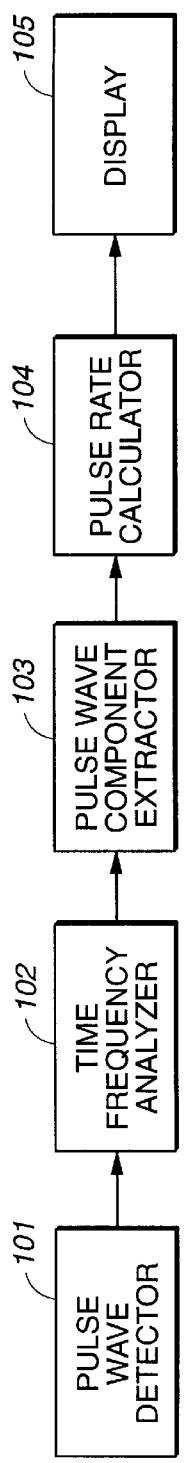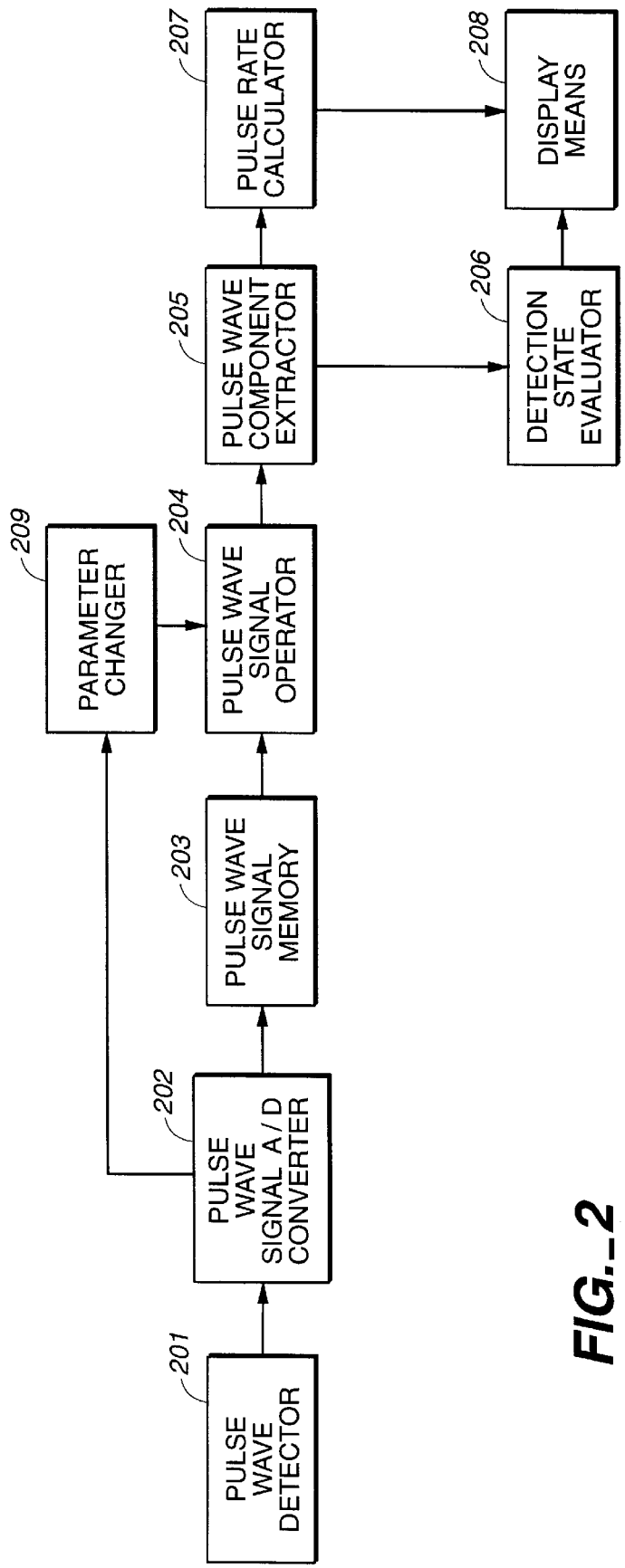
FIG._1
FIG._2

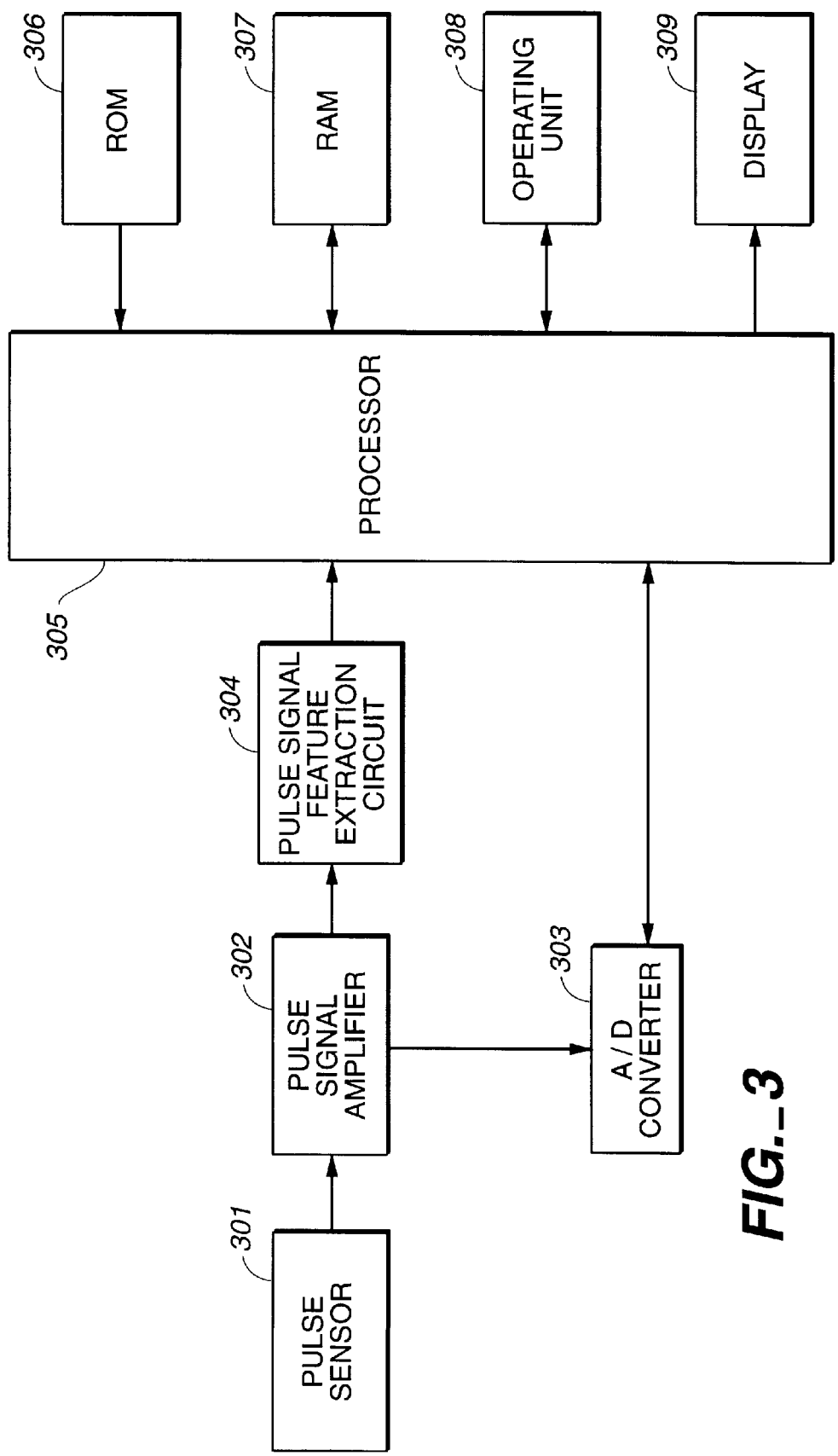
FIG._3

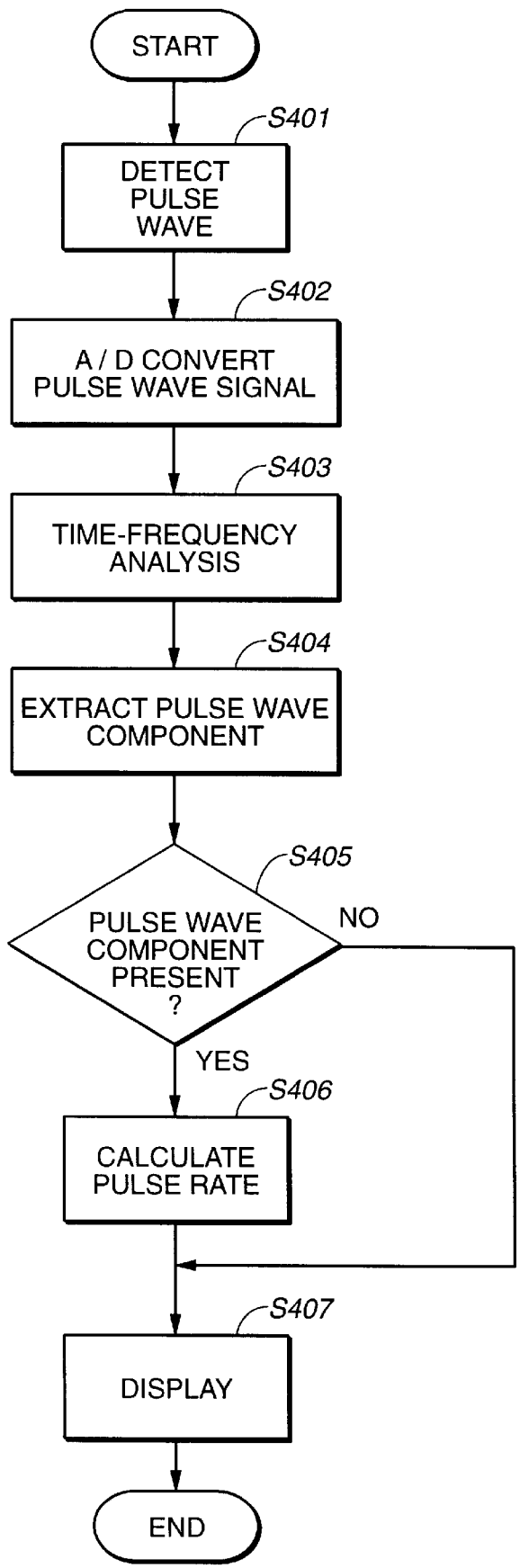
FIG._4

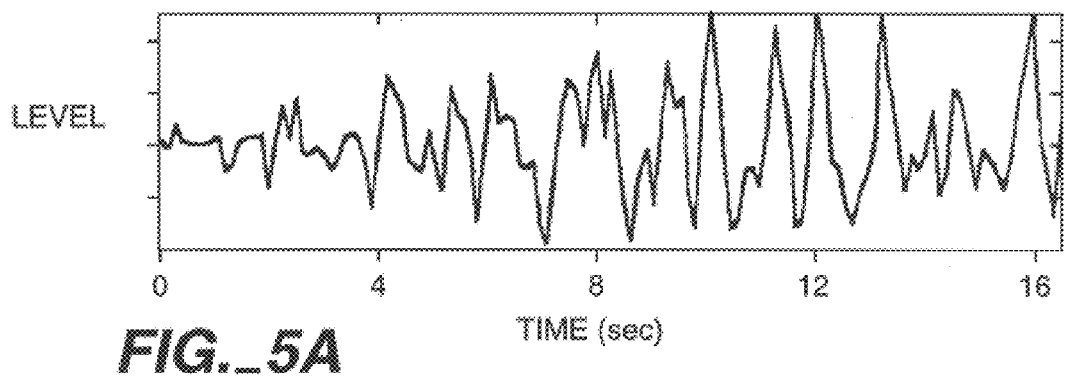
FIG._5A
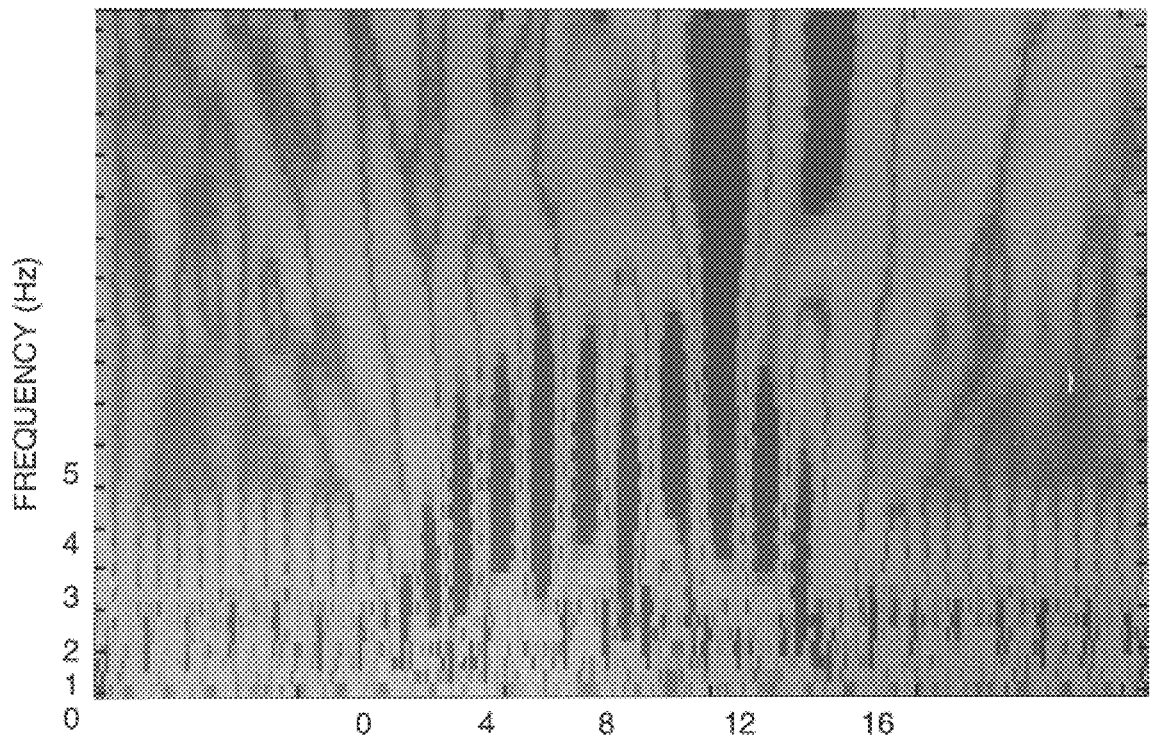
FIG._5B
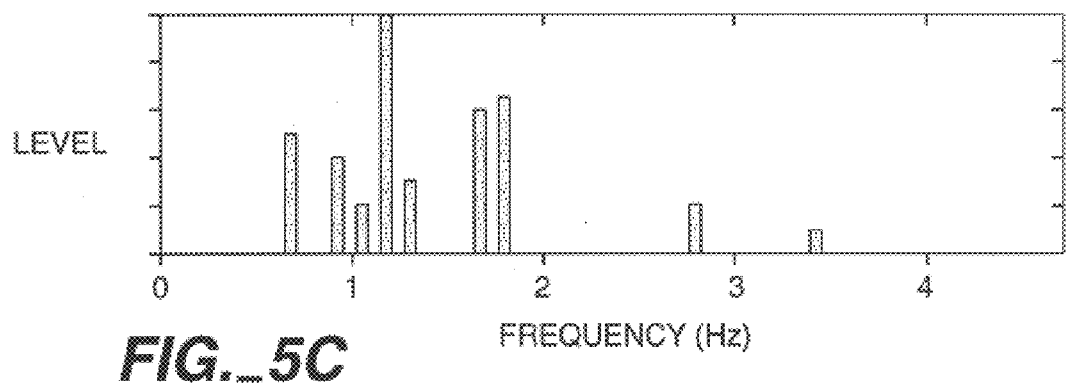
FIG._5C

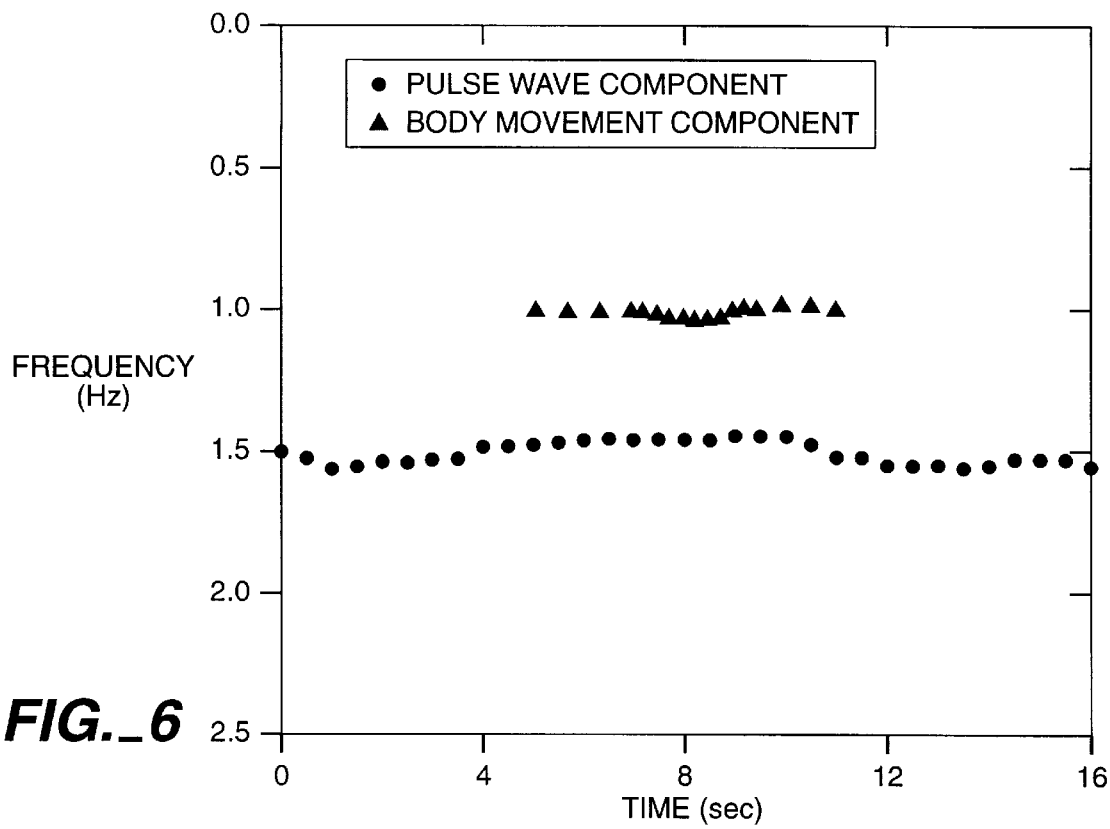
FIG._6
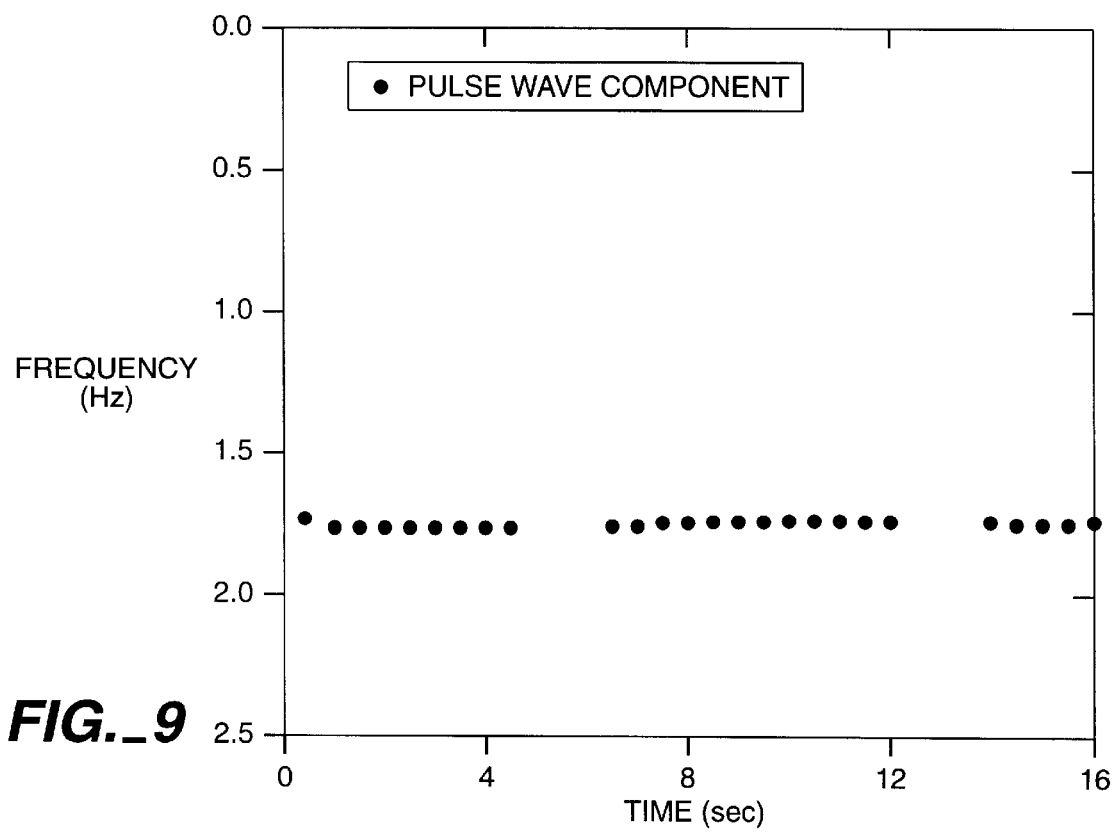
FIG._9

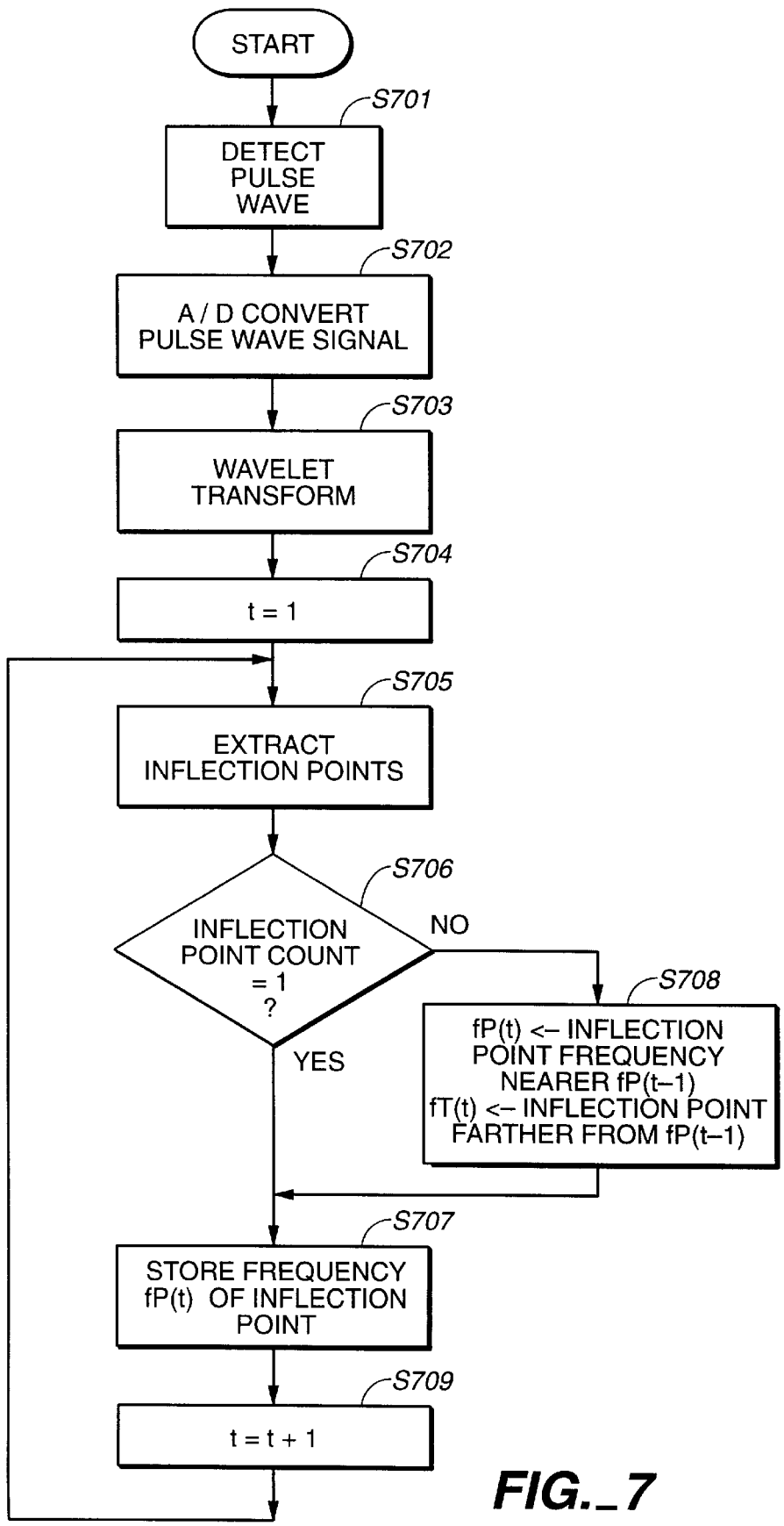
FIG._7

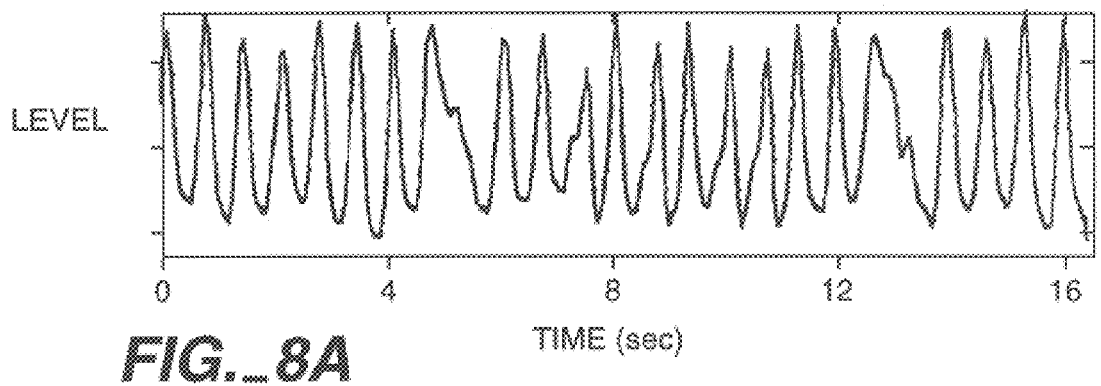
FIG._8A
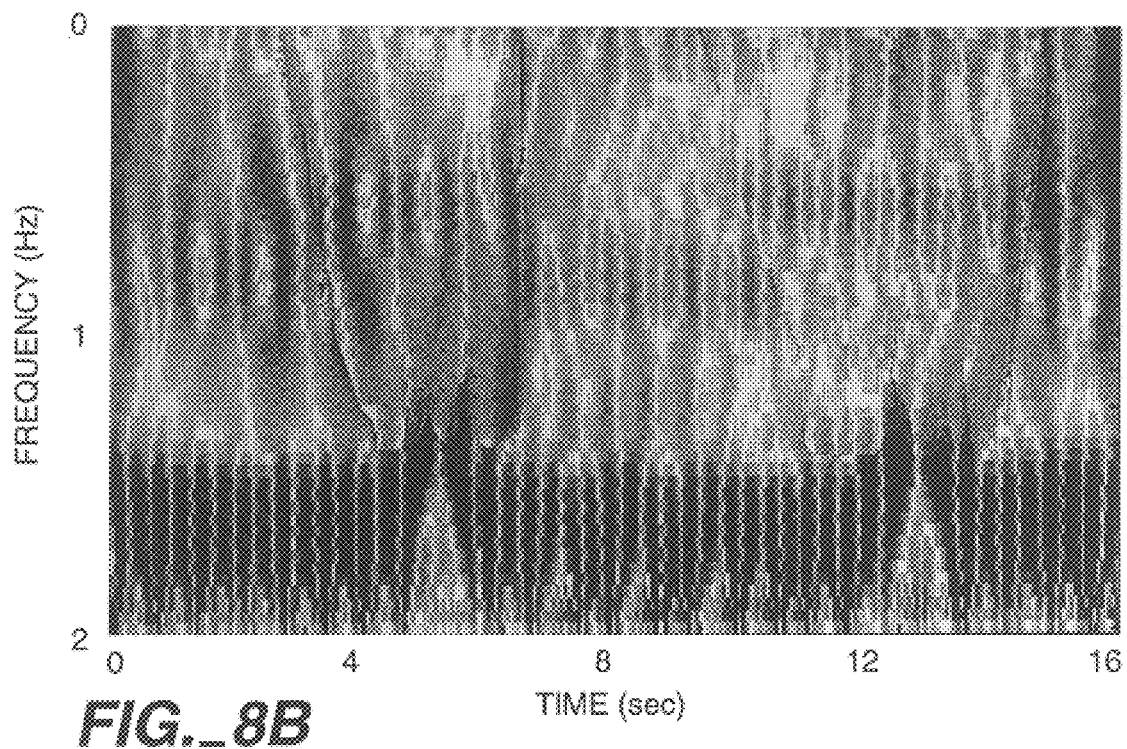
FIG._8B
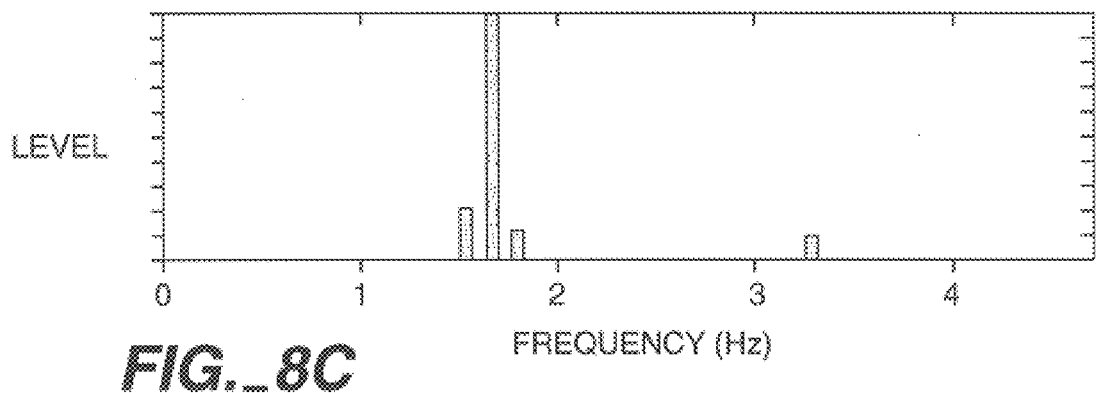
FIG._8C

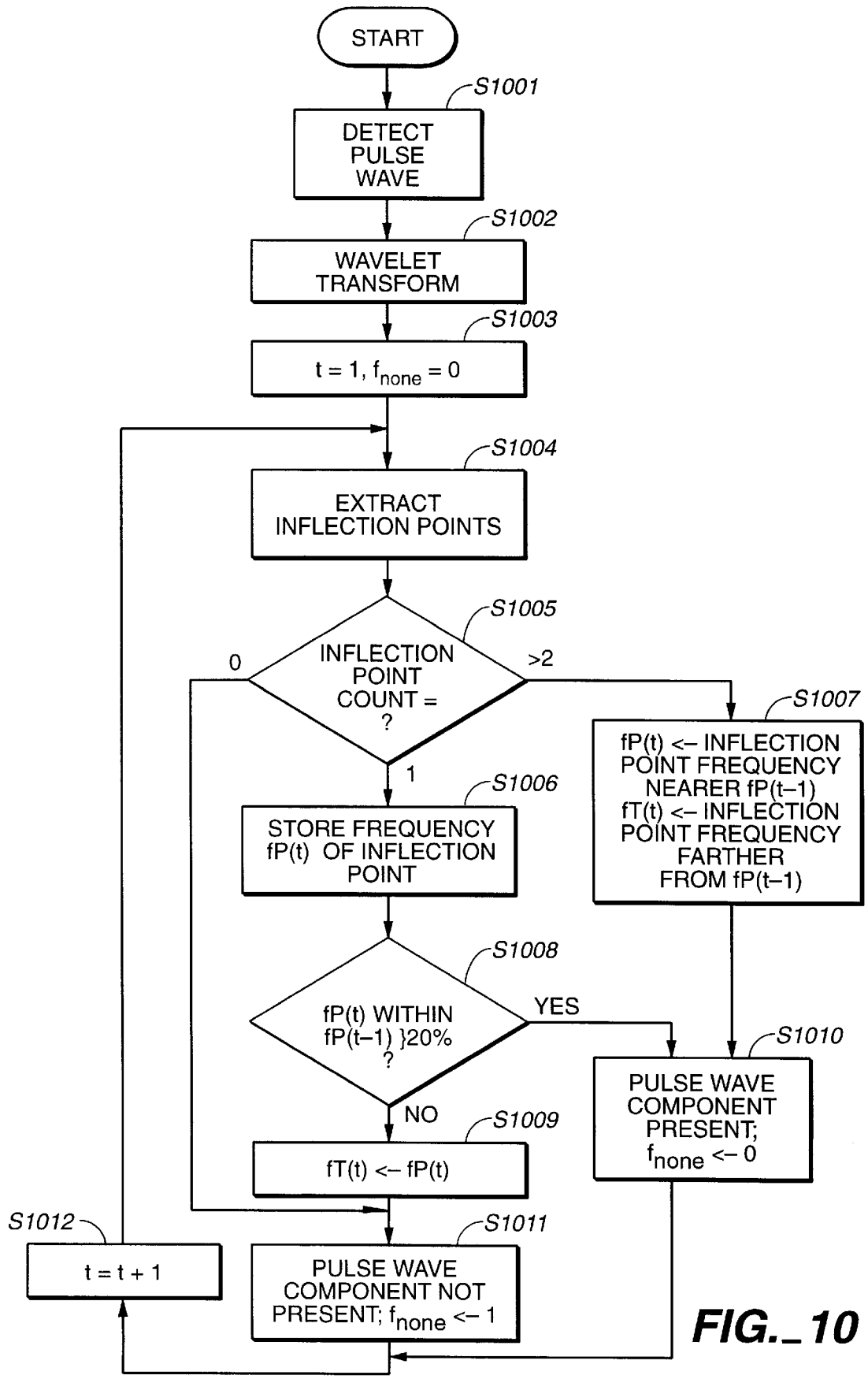
FIG._10

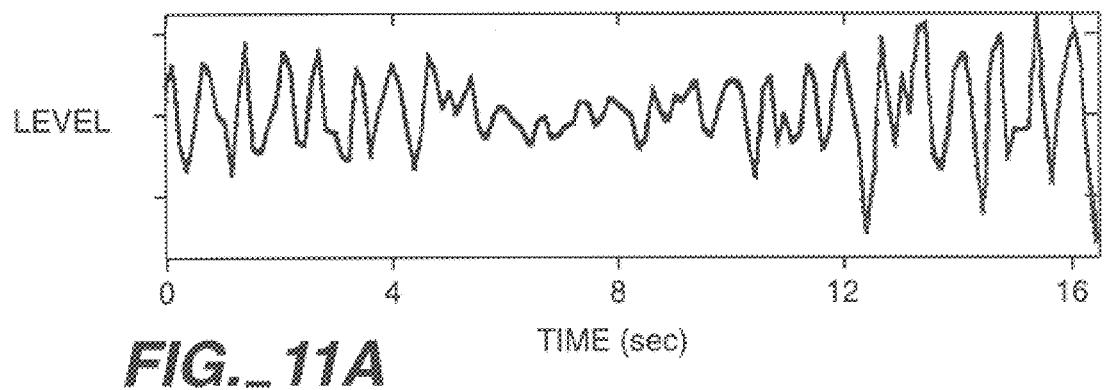
FIG._11A
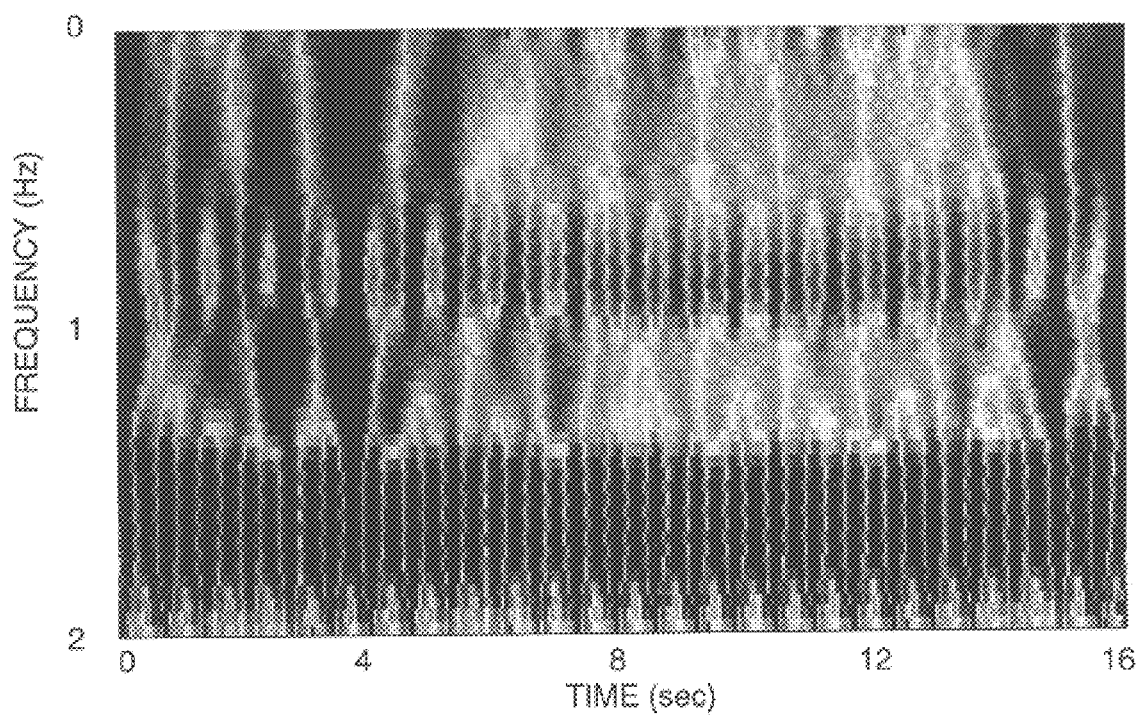
FIG._11B
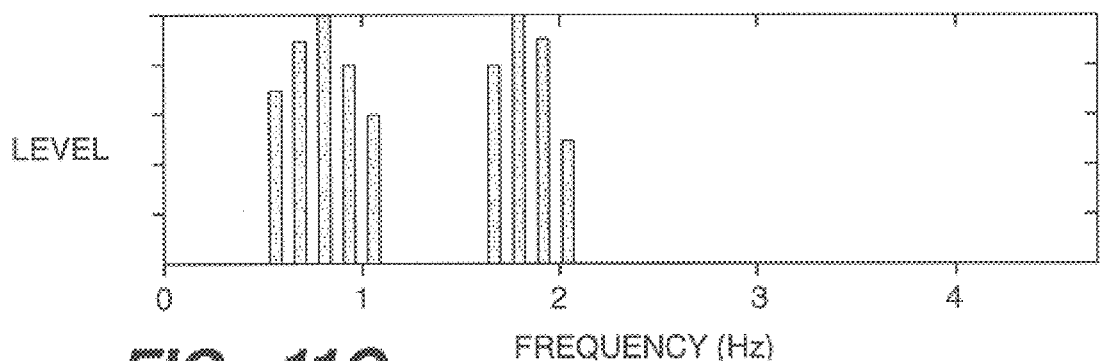
FIG._11C

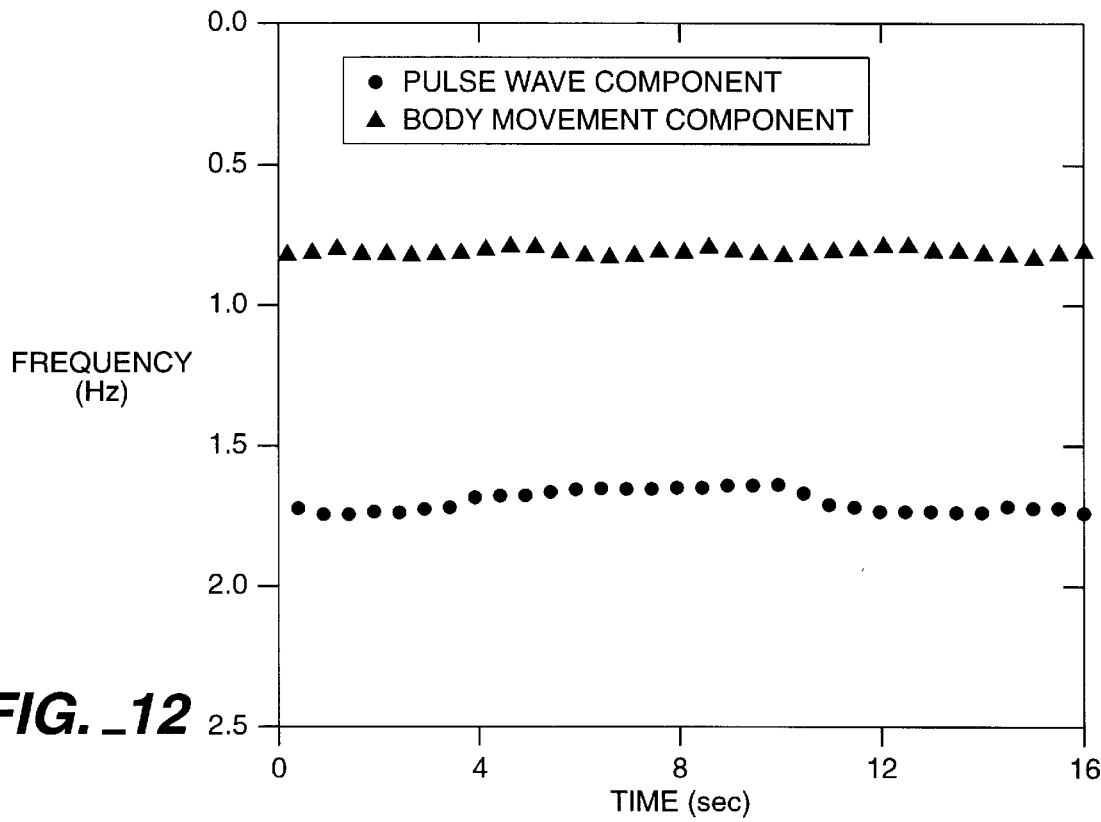
FIG._12
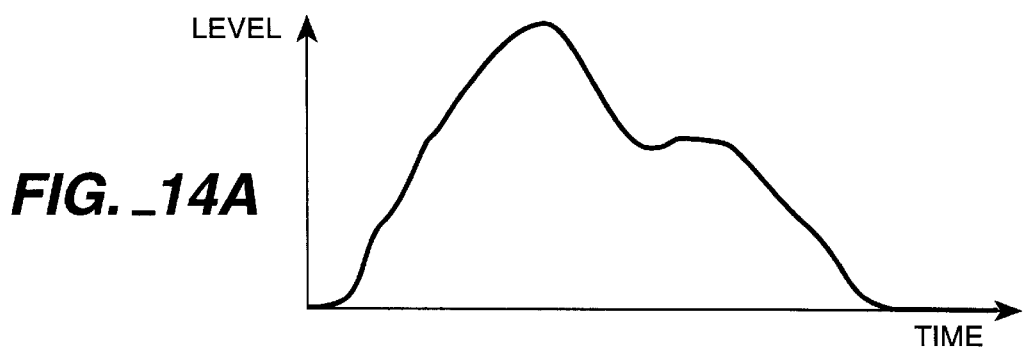
FIG._14A
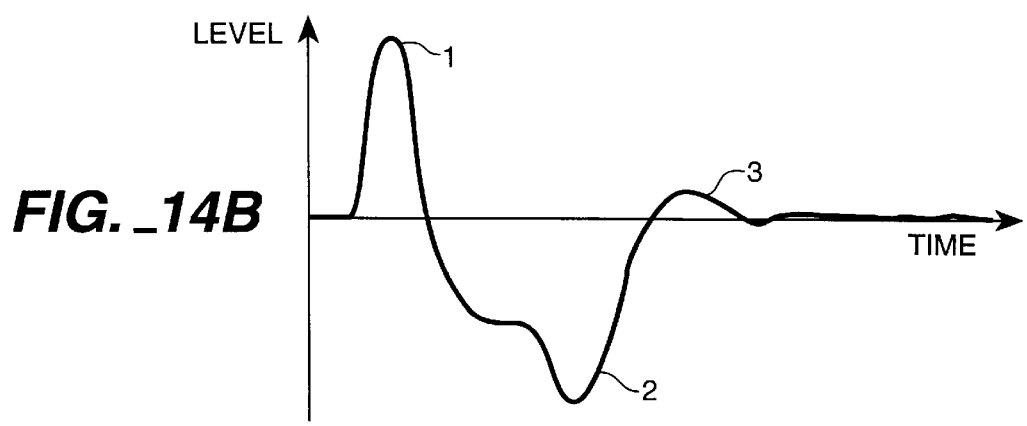
FIG._14B

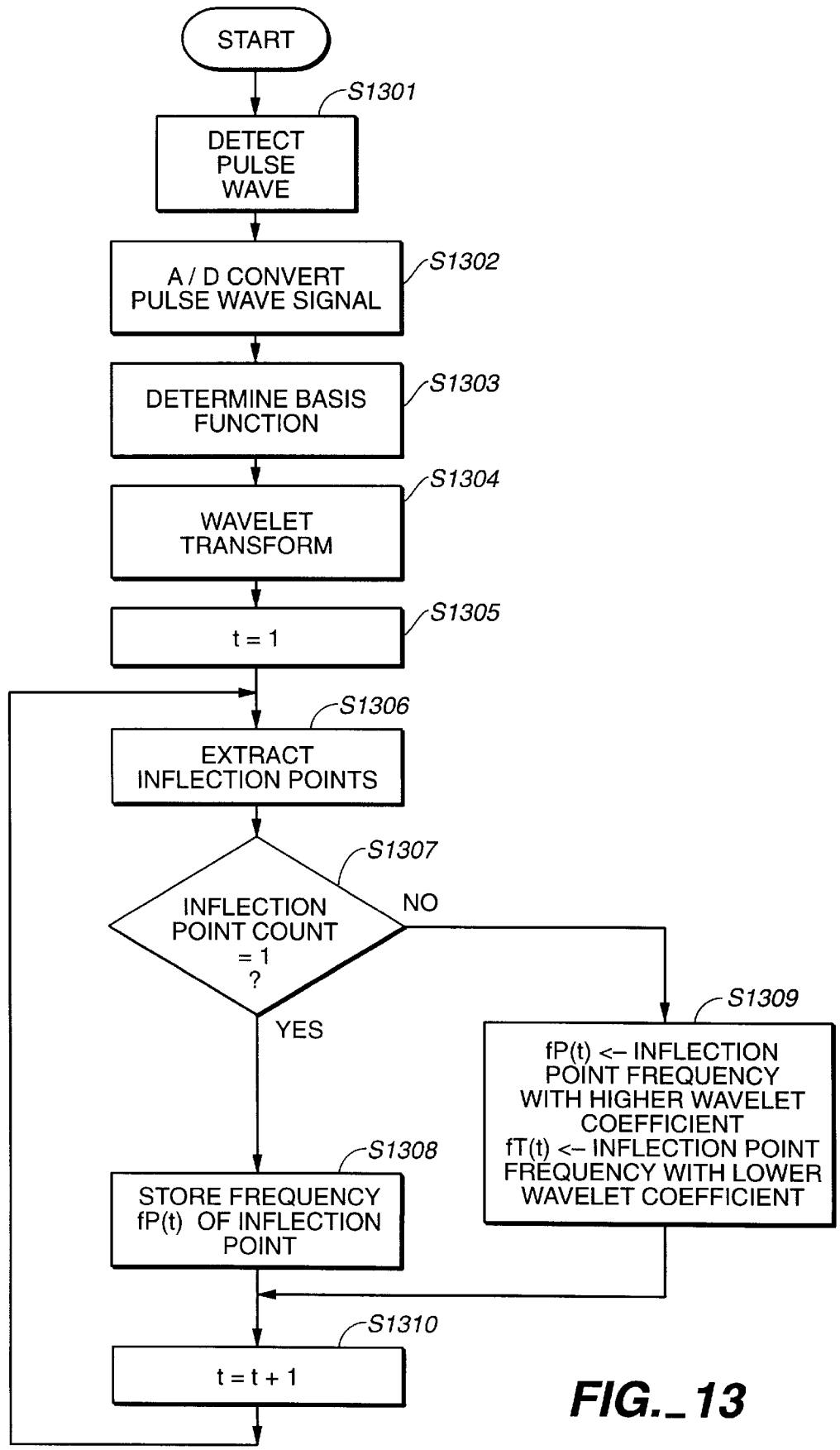
FIG._13

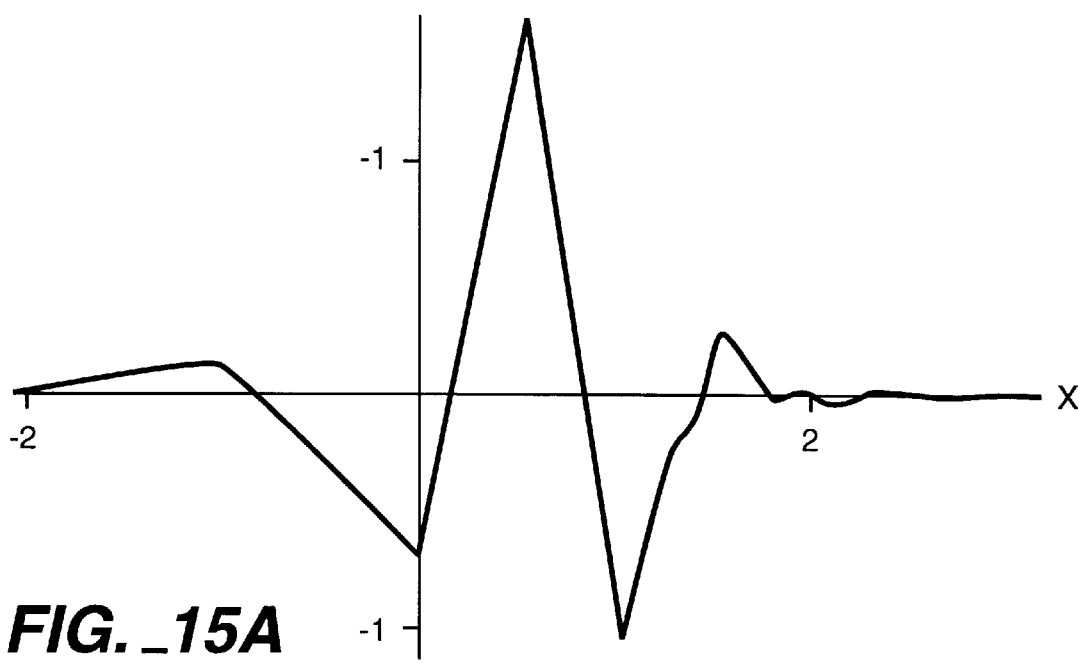
FIG._15A
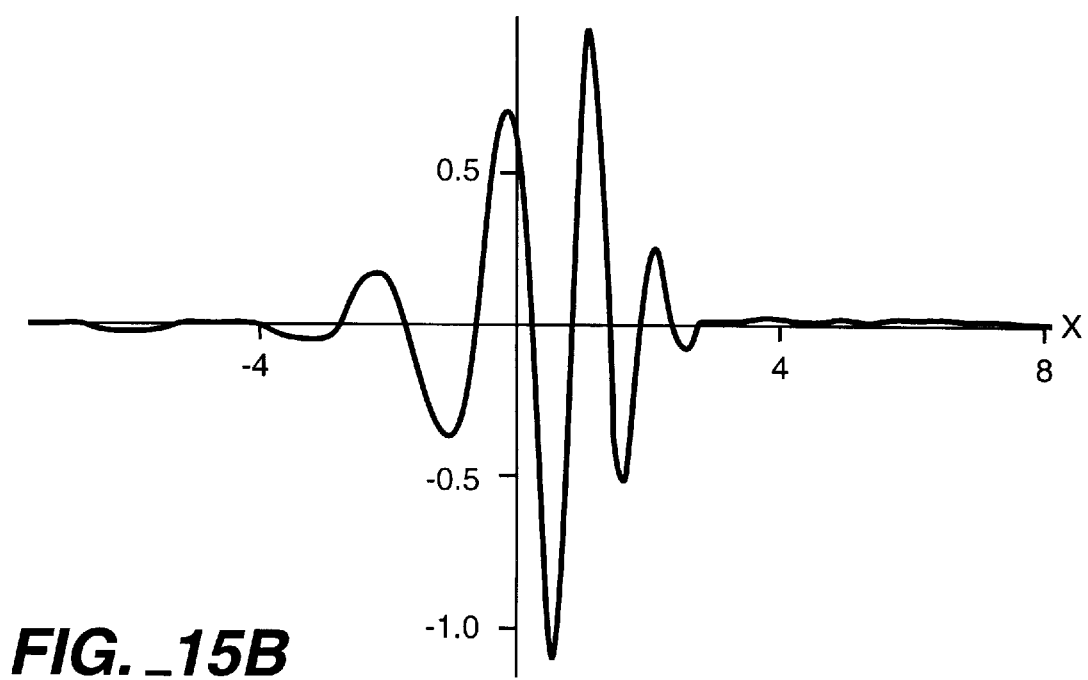
FIG._15B

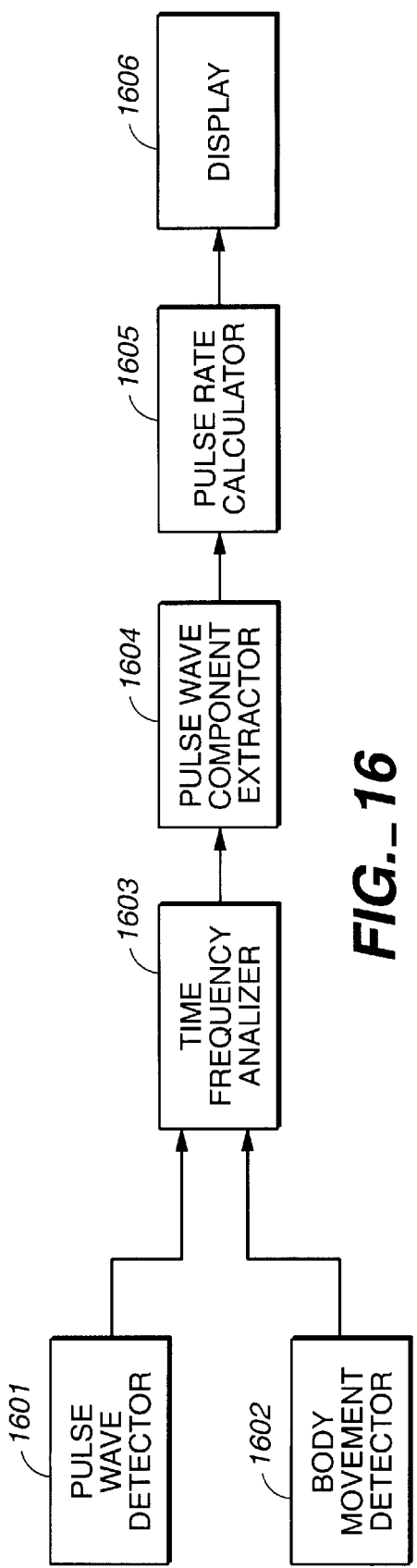
FIG._16
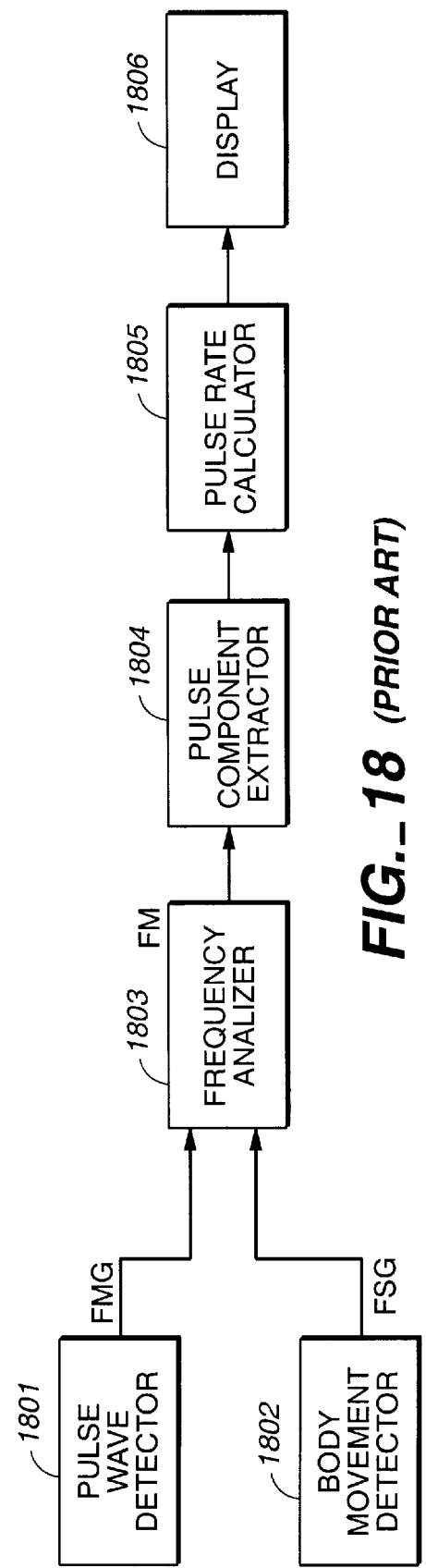
FIG._18 (PRIOR ART)

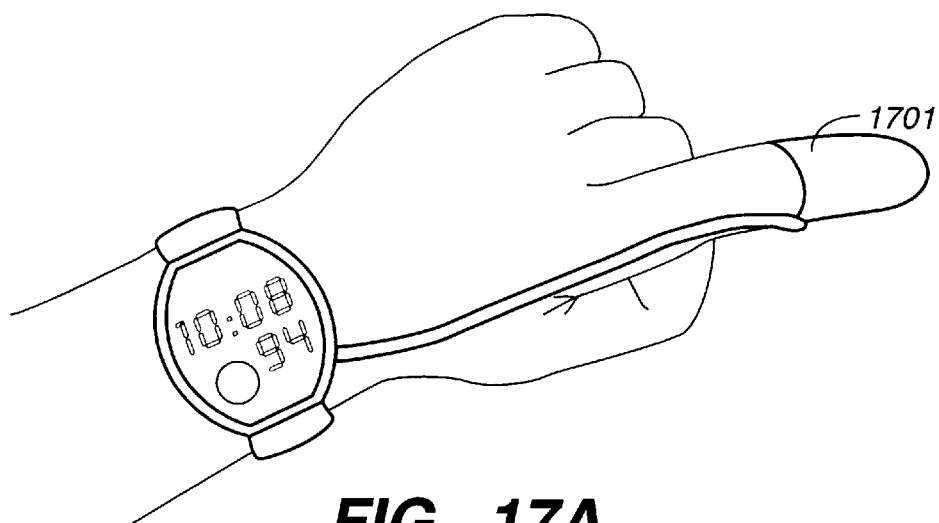
FIG._17A
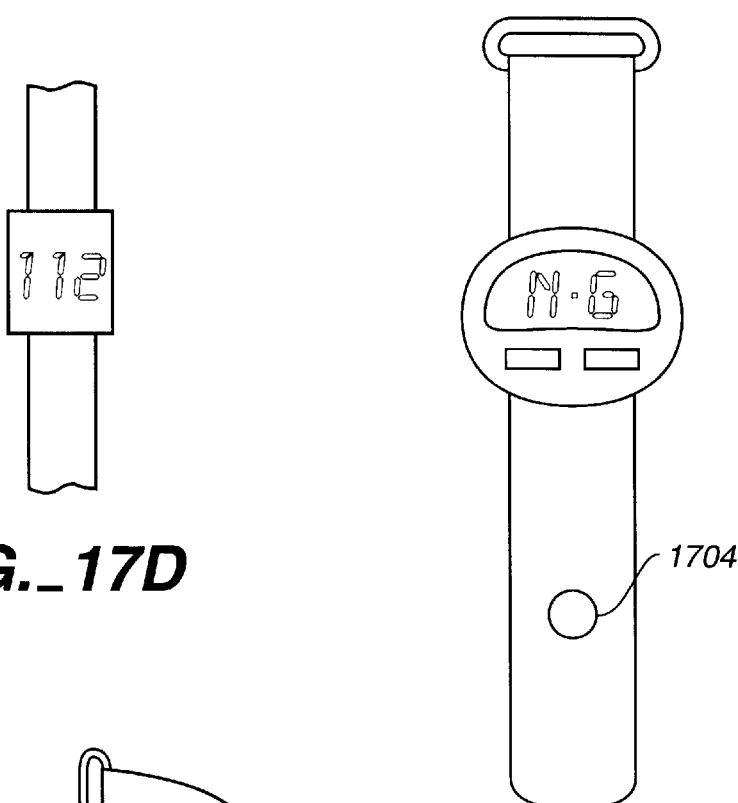
FIG._17D
FIG._17C
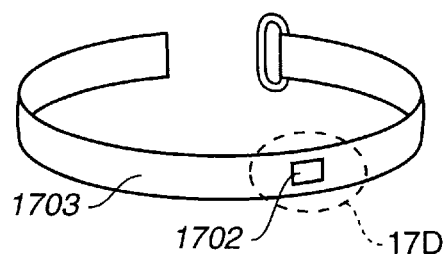
FIG._17B

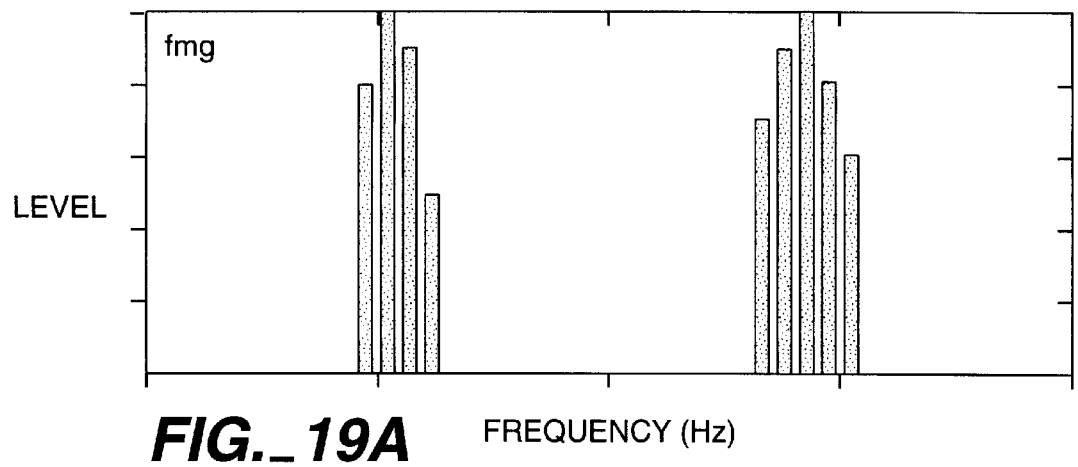
FIG._19A
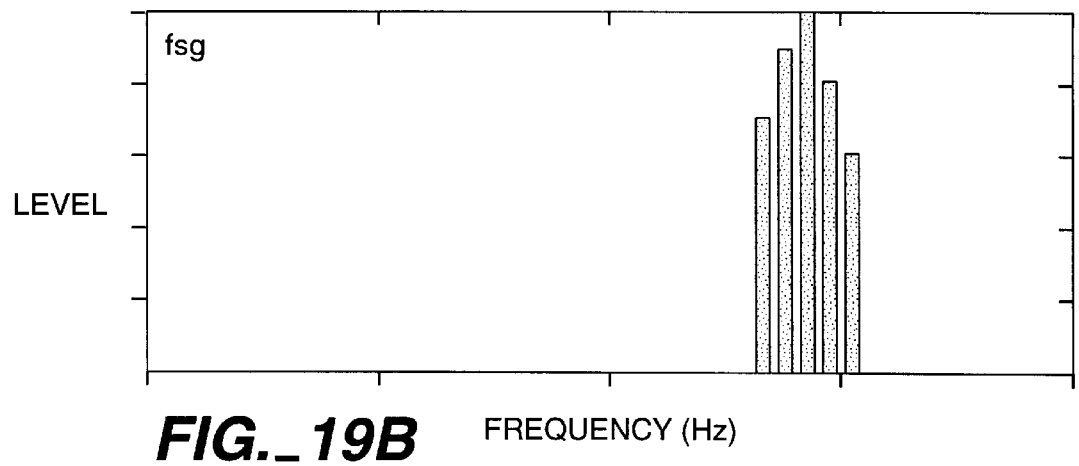
FIG._19B
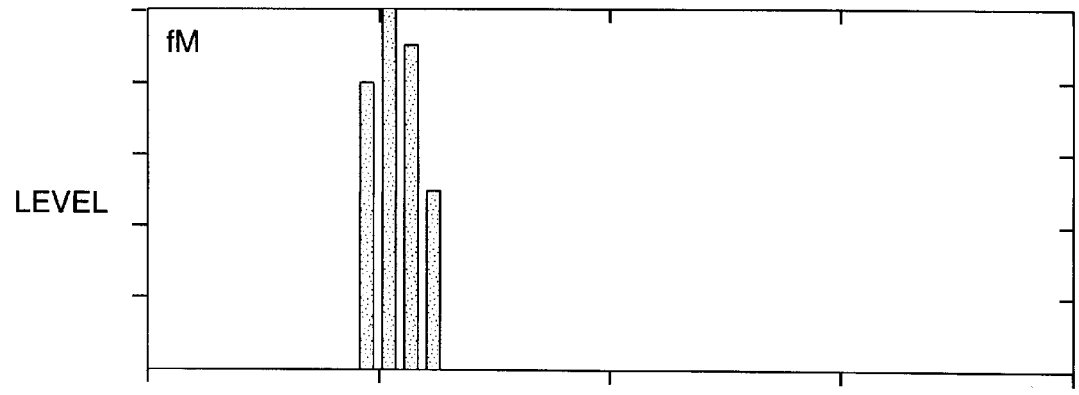
FIG._19C

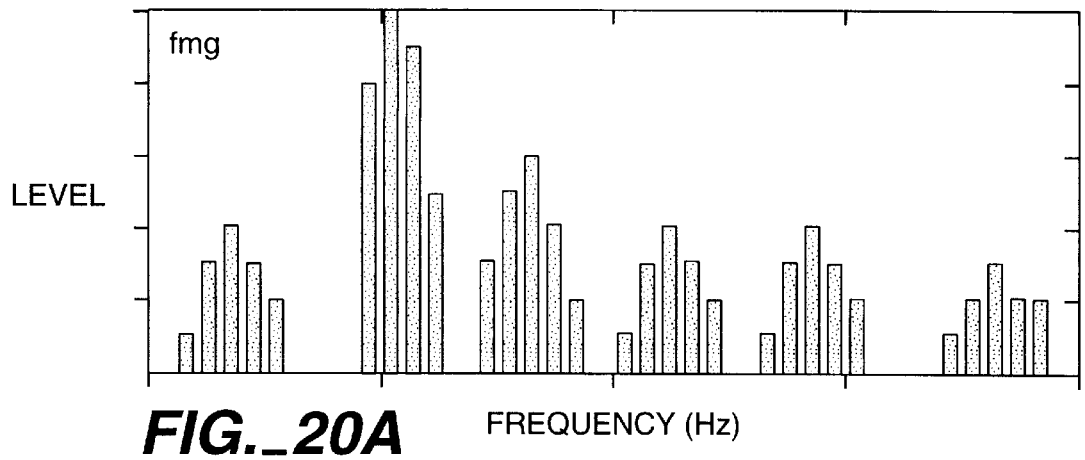
FIG._20A
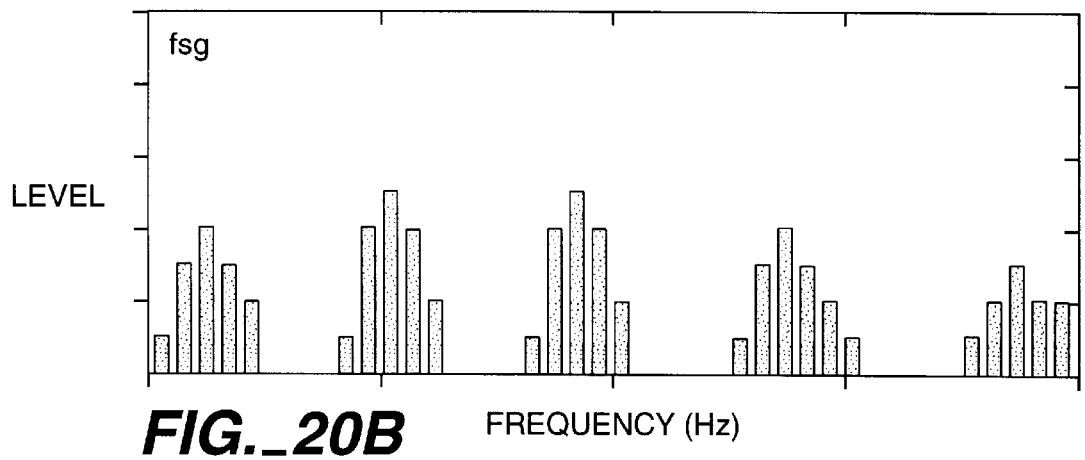
FIG._20B
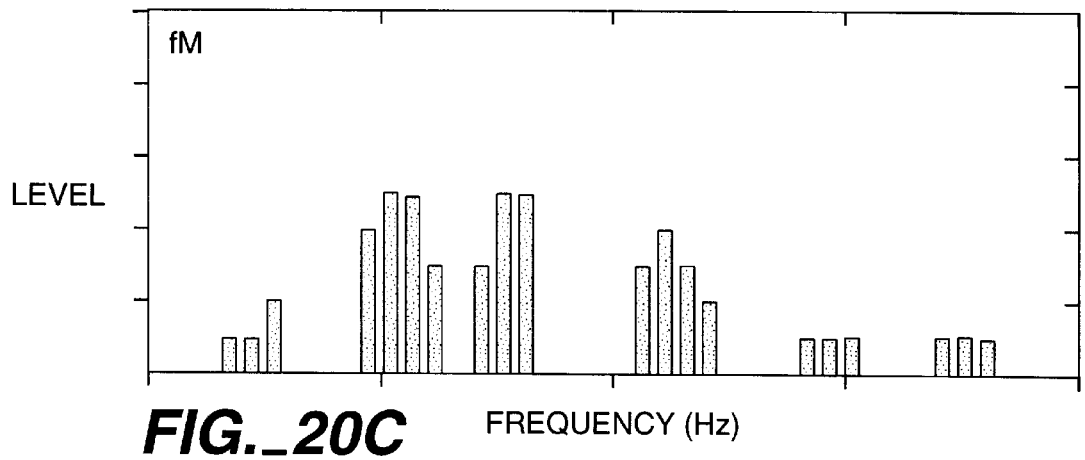
FIG._20C

PULSIMETER

BACKGROUND OF THE INVENTION

1. Field of the Invention

The present invention relates to a pulsimeter for analyzing a pulse wave signal detected from the human body.

2. Description of the Related Art

FIG. 18 is a block diagram of the functions of a pulsimeter according to related technology as described in Japan Unexamined Patent Publication 7-227383.

As shown in FIG. 18, a pulse wave detection means 1801 detects a pulse wave signal from the body of a person or user using the pulsimeter, and outputs the detected signal to a frequency analyzer 1803. A body movement detection means 1802 detects movement of the body, and likewise outputs the detected signal to the frequency analyzer 1803. Frequency analyzer 1803 then analyzes the frequency of output signals from pulse wave detector 1801 and body movement detector 1802 using, by way of example only, a fast Fourier transform operation. A pulse wave component extractor 1804 identifies a pulse wave component equivalent to the frequency of the pulse based on the result of frequency analysis of the outputs from pulse wave detection means 1801 and body movement detection means 1802, and then outputs the extracted pulse wave component to a pulse rate calculator 1805. Pulse rate calculator 1805 calculates the pulse rate per minute using the frequency component of the pulse identified by pulse wave component extraction means 1804. A display 1806 then displays the pulse rate calculated by pulse rate calculator 1805.

Note that, as described above, a pulse wave component corresponding to the pulse frequency is extracted from the result of analyzing the frequency analyzing of a detected pulse wave signal and a body movement signal, and the pulse rate per minute is then calculated from the frequency component of the pulse. Both the pulse wave signal and body movement signal are required by the apparatus described above to determine the pulse wave component.

This is described more specifically below with reference to FIGS. 19A, B and C which shows the results of a fast Fourier transform of the pulse and body movement signals obtained from a subject when walking and running, two types of exercise having a different periodic characteristic. FIG. 19A shows pulse spectrum fmg, FIG. 19B shows movement spectrum fsg, and FIG. 19C shows the extracted pulse wave component fM, i.e., the spectrum obtained by subtracting the movement spectrum fsg from the pulse spectrum fmg. As shown by these figures, the pulse spectrum fmg 19A obtained from pulse wave detector means 1801 contains both the frequency component of the pulse wave form, and the frequency component of the signal resulting from body movement. Body movement detector 1802, however, reacts only to body movement, and the detection signal output therefrom thus contains only the frequency component of the signal resulting from body movement. The movement spectrum fsg is therefore removed from the pulse spectrum fmg, and the highest remaining value in line spectrum fM is used as the frequency component of the pulse. The pulse rate is then calculated based on the frequency component of this pulse wave signal.

The results of applying a fast Fourier transform to pulse wave signals and body movement signals detected while doing aerobics, playing tennis, and other types of exercise characterized by irregular movement are shown in FIGS. 20A, B and C. FIG. 20A shows pulse spectrum fmg, FIG. 20B shows movement spectrum fsg, and FIG. 20C shows the extracted pulse wave component fM, i.e., the spectrum obtained by removing the movement spectrum fsg from the pulse spectrum fmg.

As shown in FIGS. 19A–C the period of a signal representing exercise characterized by regular periodic motion has a specific line spectrum. When the exercise is not characterized by such regular motion, however, the body movement signal does not have a readily discernible periodic component, resulting in plural line spectrums. As a result, a plurality of line spectrums remains (FIG. 20C) even after the movement spectrum fsg is subtracted from the pulse spectrum fmg, and it is therefore not easy to identify the pulse wave frequency component.

A problem with a Fourier transform using a sine wave or other periodic signal as the basis function is that frequency analysis of local signal changes, i.e., analysis with high temporal resolution, is not possible. It is therefore not possible to extract a pulse wave component from a pulse wave signal with a superposed body movement component resulting from exercise characterized by irregular movement. This problem arises because the basis function is spread uniformly.

OBJECTS OF THE INVENTION

Therefore, it is an object of the present invention to overcome the aforementioned problems.

Therefore, another object of the present invention is to provide a pulsimeter whereby a pulse wave component can be accurately and discretely extracted whether the accompanying body movement is regular (periodic) or irregular.

When the pulse wave sensor is attached to part of the body, pulse wave detection can be disabled depending upon how the pulse wave sensor is worn or attached. A further object of the present invention is therefore to provide a pulsimeter whereby it is possible to determine when pulse wave detection is not possible.

SUMMARY OF THE INVENTION

To achieve the above objects, a pulsimeter according to the present invention comprises a pulse wave component extractor to extract a pulse wave component from the result of a time-frequency analysis of a pulse wave signal obtained by a pulse wave sensor, and a pulse rate calculator for counting the pulse rate per minute based on the pulse wave component extracted by the pulse wave component extractor, and the calculated pulse rate is then displayed on a display, such as, a liquid crystal display.

The pulsimeter of the invention preferably further comprises a parameter changer circuit for changing a parameter of a basis function used for the time-frequency analysis to a value facilitating pulse wave component extraction.

A detection state evaluator is further provided for evaluating the presence of a pulse wave component in the result output by the pulse wave component extractor. As a result, the detection state of the pulse wave sensor can be displayed.

An exemplary method of time-frequency analysis uses a wavelet transform method to represent a signal in terms of a wavelet function, and then apply time-frequency analysis using a wavelet coefficient. Wavelet functions are localized in both frequency and time, and information relating to the time and frequency characteristics of a signal can therefore be obtained from the wavelet coefficients. A wavelet function is obtained by scale conversion and time-base shifting of the wavelet basis function. High resolution can then be achieved by using this localized basis function.

Other objects and attainments together with a fuller understanding of the invention will become apparent and appreciated by referring to the following description and claims taken in conjunction with the accompanying drawings.

BRIEF DESCRIPTION OF THE INVENTION

In the drawings wherein like reference symbols refer to like parts.

FIG. 1 is a functional block diagram of a pulsimeter in accordance with an embodiment of the present invention;

FIG. 2 is a functional block diagram of another pulsimeter in accordance with an embodiment of the present invention;

FIG. 3 is a schematic diagram of the pulsimeter of FIG. 1;

FIG. 4 is a flow chart illustrating the operation of the pulsimeter in accordance with a first embodiment of the present invention;

FIG. 5A is a sample of a wave form to which a wavelet transform operation is applied;

FIG. 5B illustrates the result of a wavelet transform of the signal shown in FIG. 5A; and FIG. 5C shows the result of a fast Fourier transform of the signal shown in FIG. 5A;

FIG. 6 is a graph of inflection points extracted from FIG. 5B;

FIG. 7 is a flow chart describing a method used by a pulsimeter in accordance with the first embodiment of the present invention for extracting a pulse wave component;

FIG. 8A is a sample of a wave form to which a wavelet transform operation is applied;

FIG. 8B shows the result of the wavelet transform of the signal shown in FIG. 8A; and FIG. 8C shows the result of a fast Fourier transform of the signal shown in FIG. 8A;

FIG. 9 is a graph of the inflection points extracted from FIG. 8B;

FIG. 10 is a flow chart describing a method used by a pulsimeter in accordance with a second embodiment of the present invention for extracting a pulse wave component;

FIG. 11A is a sample of a wave form to which a wavelet transform operation is applied;

FIG. 11B shows the result of the wavelet transform of the signal shown in FIG. 11A; and FIG. 11C shows the result of a fast Fourier transform of the signal shown in FIG. 11A;

FIG. 12 is a graph of the inflection points extracted from FIG. 11B;

FIG. 13 is a flow chart describing a method used by a pulsimeter in accordance with a third embodiment of the present invention for extracting a pulse wave component;

FIG. 14A is a sample of a pulse wave signal;

FIG. 14B shows the graphed second differential of the signal in FIG. 14A;

FIG. 15A is a graph of Daubechies basis function for N=3, and

FIG. 15B is a graph of Daubechies basis function for N=8;

FIG. 16 is a functional block diagram of a pulsimeter according to a further embodiment of the present invention;

FIGS. 17 A–D show possible embodiments of a pulsimeter according to the present invention, FIG. 17A illustrates a pulse wave sensor comprised in a finger sack, FIG. 17B showing a pulse wave sensor held by a belt, and FIG. 17C showing a pulse wave sensor held in a watch band;

FIG. 17D is a detailed view of the pulsimeter of FIG. 17B;

FIG. 18 is a functional block diagram of a conventional pulsimeter;

FIG. 19A is a graph of the results of a fast Fourier transform of pulse wave sensor output during exercise characterized by cyclical (regular) motion, FIG. 19B is a graph of the results of a fast Fourier transform of body motion sensor output during the same exercise, and FIG. 19C shows the difference between the results graphed in FIGS. 19A and 19B; and FIG. 20A is a graph of the results of a fast Fourier transform of pulse wave sensor output during exercise characterized by irregular motion, FIG. 20B is a graph of the results of a fast Fourier transform of body motion sensor output during the same exercise, and FIG. 20C shows the difference between the results graphed in FIGS. 20A and 20B.

DESCRIPTION OF THE PREFERRED EMBODIMENTS

FIG. 1 is a functional block diagram of a first embodiment of a pulsimeter according to the present invention. Referring to FIG. 1, a pulse wave detector 201 or pulse wave detection means detects a pulse wave signal from the body, and outputs the detected signal to a time-frequency analyzer 102 or time-frequency analyzer means. The time-frequency analyzer 102 thus time-frequency analyzes the output signal from pulse wave detector 101 using, by way of example only, a wavelet transform for time-frequency analysis. A pulse wave component extractor 103 or pulse wave component extraction means then identifies a pulse wave component equivalent to the frequency of the pulse based on the result of the time-frequency analysis of the output signal from pulse wave detector 101, and outputs the detected pulse wave component to a pulse rate calculator 104 or pulse rate calculation means. The pulse rate calculator 104 calculates the pulse rate per minute using the frequency component of the pulse identified by pulse wave component extractor 103. A display 105 or display means, then displays the pulse rate calculated by pulse rate calculator 104. The display can of course be any suitable display such as an LCD, LED and the like.

FIG. 2 is a functional block diagram of a pulsimeter according to a first embodiment of the present invention. In this embodiment a pulse wave detector 201 or pulse wave detection means outputs an analog voltage signal representing the detected body pulse. A pulse wave signal analog to digital (A/D) converter 202 or pulse wave conversion means then extracts the pulse wave signal and converts this analog signal to a digital signal, which it outputs to a pulse wave signal memory 203 and a parameter changer 209 or parameter changing means. Pulse wave signal memory 203 or pulse wave storage means stores the digitally converted pulse wave signal.

Based on the extracted pulse wave signal supplied from pulse wave signal A/D converter 202, parameter changer 209 appropriately changes a parameter of a function used by pulse wave signal operator 204 or pulse wave signal operating means.

Pulse wave signal operator 204 or pulse wave signal operating means sequentially reads and time-frequency analyzes the pulse wave signals stored to pulse wave signal memory 203, and outputs a result of this analysis to a pulse wave component extractor 205 or pulse wave component extraction means. Pulse wave component extractor 205 extracts only the pulse wave component from the result of time-frequency analysis output by pulse wave signal operator 204.

Using the frequency component of the pulse wave extracted by pulse wave component extractor 205, detection state evaluator 206 determines the time a pulse wave is not present, and outputs a signal to display 208 during this period.

A pulse rate calculator 207 calculates the pulse rate per minute from the frequency component of the pulse wave extracted by pulse wave component extractor 205, and outputs the result to display 208. Display 208 displays the pulse rate supplied from pulse rate calculator 207 and the evaluation result output from detection state evaluator 206.

The preferred embodiments of the present invention are described in further detail below with reference to the accompanying drawings.

First Embodiment

FIG. 3 is a schematic diagram of the functions of the first embodiment of a pulsimeter according to the present invention.

Referring to FIG. 3, a pulse wave sensor 301 detects a pulse of a user, and outputs the detected pulse wave signal to a pulse wave signal amplifier 302. Note that an exemplary embodiment of pulse wave sensor 301 can be a piezoelectric microphone, a photoelectric sensor, or an ultrasonic sensor. Pulse wave signal amplifier 302 amplifies the pulse wave signal, and outputs to a analog to digital (A/D) converter 303 and pulse wave signal feature extraction circuit 304. A/D converter 303 converts the analog pulse wave signal to a digital signal which is supplied to processor (CPU) 305. Pulse wave signal feature extraction circuit 304 differentiates the pulse wave signal to obtain the inflection point count which is output to CPU 305. CPU 305 controls the operation of the pulsimeter. The program used by processor 305 is stored in a computer readable medium such as a nonvolatile memory for example ROM 306. Additionally any parameters are also stored in ROM 307. Volatile memory, such as RAM 307 is provided to temporarily store instructions of the program used by processor 305 during execution, during time-frequency analysis, extraction and pulse rate calculation sub processes. Additionally RAM 305 stores the measured pulse wave data.

Operating unit 308 is implemented as a numeric coprocessor to perform time-frequency analysis. As can be appreciated by one of ordinary skill in the art, time-frequency analysis is computation intensive. In the preferred embodiment in order to reduce the computing burden on CPU 305, the inventors have provided operating unit 308.

The program executed by CPU 301 is set forth in the method described below. It will be appreciated that one of ordinary skill in the art is capable of developing the appropriate software in accordance with the method described below, the processor, and operating system selected.

FIG. 4 is a flow chart referred to below to describe the operation of a pulsimeter according to the present invention from pulse wave detection to pulse rate calculation and display. Referring to both FIGS. 3 and 4, the detected pulse wave signal (S401) is converted from an analog signal to a digital by A/D converter 303 (S402), and the resulting data is input to CPU 305. Operations unit 308 time-frequency analyzes (S403) (in accordance with the programmed instructions in RAM 302) the received data using a wavelet transform in an exemplary embodiment of the invention, and extracts a frequency component of the pulse wave (S404).

CPU 305 determines whether there is a period during which a pulse wave component is not present (S405). If the result of this step is no as shown in FIG. 4, CPU 305 displays an indication that a pulse wave component is not present (S407). If a pulse wave component is detected (S405 returns yes), CPU 305 calculates the pulse rate from the extracted pulse wave component (S406), and then displays the pulse rate (S407).

A pulse wave signal obtained from a subject while exercising, such as aerobics, is characterized by irregular motion is shown in FIG. 5A. Time seconds is shown on the horizontal axis in FIG. 5A with 128 sampling points obtained at 0.125 second intervals over a 16 second detection period plotted. The pulse wave signal level obtained by A/D conversion of the pulse wave signal potential is shown on the vertical axis.

The result of applying a wavelet transform to the wave shown in FIG. 5A using Symlets function as the wavelet basis function is shown in FIG. 5B. As in FIG. 5A, time seconds is shown on the horizontal axis while frequency (Hz) is shown on the vertical axis. Shading in the graph indicates the relative level of the wavelet coefficient after wavelet transform; shading darkens as the coefficient level rises. As the level rises, the frequency component population at that point also rises. As a result, the frequency distribution of the pulse wave signal at each sampling time can be determined. This makes it possible to isolate the body movement component, which is represented by local frequency changes, mixed with the pulse wave component and pulse wave signal.

The result of a fast Fourier transform (FFT) applied to the pulse wave signal in FIG. 5A is shown in FIG. 5C. Note that there is no time reference, resulting in an average frequency distribution for the 16 second detection period. The FFT result is therefore not compatible with detection of local changes in frequency.

The result of pulse wave component extraction from the wavelet transform result shown in FIG. 5B is shown in FIG. 6. As in FIGS. 5A and FIG. 5B, time second is shown on the horizontal axis, and 128 samples were taken at 0.125 second intervals. The inflection point of the frequency was extracted at discrete time points in the wavelet transform result (FIG. 5B), and plotted on the vertical axis in FIG. 6. When there is only one inflection point at a given time in FIG. 6, only the pulse wave component is present; when there are two inflection points at a particular time, such as shown in the period from approximately 5 seconds to 11 seconds, a body movement component is superposed on the pulse wave component.

An exemplary process for extracting the pulse wave component using a wavelet transform is described next below with reference to FIG. 7. As described above, a pulse wave signal is detected from the body (S701), and then converted from an analog signal to a digital signal for quantization (S702). A wavelet transform operation is then applied (S703). A sampling point counter t is then initialized to t=1 (S704); sampling time is obtained as the sampling interval times t.

Based on the wavelet transform result, the inflection points are extracted from the frequency distribution at each sampling time (S705). The number of inflection points at each sampling time is then counted. If there is only one inflection point, it is determined that the body is in a state of rest with no body movement component superposed on the detection signal, and that there is, therefore, only a pulse wave component present (S706). The frequency fP(t) of the inflection point at this time is therefore stored (S707), i.e., fP(t) is the current pulse rate.

If there are two or more inflection points detected (S706), both a pulse wave component and body movement component are present. The inflection point frequency closer to the previous frequency fP(t−1) is therefore detected as frequency fP(t). The inflection point frequency farther from the previous frequency fp(t−1) can be determined to represent the frequency of body movement, and is therefore defined stored as frequency fT(t) (S708). The frequency detected as frequency fP(t) is then stored (S707), and sampling point counter t is then incremented to detect the inflection point count and frequency at the next sampling time (S709). By thereafter repeating this loop from S705 to S709, the pulse rate can be sequentially determined.

Second Embodiment

A pulsimeter according to a second embodiment of the present invention is described next below. The schematic diagram for this second embodiment is also shown in FIG. 3, and is identical to that of the first embodiment above. The program executed by CPU 305 is described below and is shown in FIG. 10.

When a body movement signal is superposed on a pulse wave signal, the pulse wave signal can be buried in the body movement signal when the body movement signal is particularly strong. In certain cases it is also not possible to extract the pulse wave component. This can occur in the following cases:

(1) the body movement component is large, and the pulse wave component is buried as a result;
(2) the pulse wave sensor cannot detect the pulse from the body;
(3) the pulse itself is weak or irregular.

A pulse wave signal obtained by detection of an irregular pulse with the subject at rest is shown in FIG. 8A as exemplary of case (3) above. As in FIG. 5, (seconds) is shown on the horizontal axis in FIG. 8A with 128 sampling points obtained at 0.125 sec intervals over a 16 second detection period plotted. The pulse wave signal level obtained by A/D conversion of the pulse wave signal potential is shown on the vertical axis.

The result of applying a wavelet transform to the wave shown in FIG. 8A using Daubechies function as the basis function is shown in FIG. 8B. As in FIG. 8A, time seconds is shown on the horizontal axis while frequency (Hz) is shown on the vertical axis. Shading in the graph indicates the relative level of the wavelet coefficient after wavelet transform; shading darkens as the coefficient level rises. As the level rises, the frequency component population at that point also rises. As a result, the frequency distribution of the pulse wave signal at each sampling time can be determined, thereby enabling the pulse wave component distribution and the body movement component distribution to be determined.

The result of a fast Fourier transform applied to the pulse wave signal in FIG. 8A is shown in FIG. 8C. Note that there is no time reference, resulting in an average frequency distribution for the 16 second detection period. The FFT result is therefore not compatible with detection of local changes in frequency, and the pulse cannot be identified as an irregular pulse.

The result of pulse wave extraction from the wavelet transform result shown in FIG. 8B is shown in FIG. 9. As in FIGS. 8A and 8B, time second is shown on the horizontal axis, and 128 samples were taken at 0.125 second intervals. The inflection point of the frequency extracted at each sampling time from the wavelet transform result (FIG. 8B) is plotted on the vertical axis in FIG. 9. The presence of only one inflection point at a given time in FIG. 9 indicates that a pulse wave component is present; the absence of a point of inflection at a particular time, such as near approximately 6 seconds to 13 seconds, indicates that a pulse wave component is not present.

An exemplary process for determining the period in which the pulse wave component is not present is described next below with reference to the flow chart in FIG. 10. Note that the cause for why the pulse wave component is not present is not specifically determined to be factor (1), (2), or (3) above.

As described above, a pulse wave signal is detected and then converted from an analog signal to a digital signal (S1001). A wavelet transform operation is then applied (S1002). A sampling point counter t is then initialized to t=1 (S1003); sampling time is obtained as the sampling interval times t. A pulse wave component presence flag $f_{none}$, which is set to 1 when it is determined that the pulse wave component is not present, is also initialized to $f_{none}$=0 (S1003).

Based on the wavelet transform result, the inflection point is extracted from the frequency distribution at each sampling time (S1004). The number of inflection points at each sampling time is then counted (S1005). If the number of inflection points is zero, a pulse wave component and body movement component are not present, and $f_{none}$ is therefore set to one ($f_{none}$=1) (S1011). If the inflection point count is 1 (S1005), however, a pulse wave component or body movement component is present. Which component is present is therefore evaluated.

The frequency of the inflection point at this time is therefore defined as frequency fP(t) (S1006). To determine whether the inflection point represents a pulse wave component or body movement component, frequency fP(t) is compared with the frequency fP(t−1) of the previously detected pulse wave component. In an exemplary embodiment of the invention, the standard for determining whether an inflection point is a pulse wave component is whether frequency fP(t) is, for example, ±20% of frequency fP(t−1) (S1008). If frequency fP(t) is ±20% of frequency fP(t−1), and the sampling point is therefore determined to be a pulse wave component, $f_{none}$ is set to zero ($f_{none}$=0) (S1010). This enables fP(t) to be converted as the current pulse rate.

If frequency fP(t) is greater than ±20% of frequency fP(t−1), the sampling point is determined to be a body movement component (S1009), and a pulse wave component is additionally determined not present. Frequency fP(t) is therefore defined stored as frequency fT(t) (S1009), and $f_{none}$ is set to one ($f_{none}$=1) (S1011).

If the inflection point count is 2 or greater (S1005), both a pulse wave component and body movement component are present. Which inflection point represents a pulse wave component and which represents a body movement component is therefore determined. The inflection point of which the frequency is closer to the previous frequency fP(t−1) is determined to represent the pulse wave component, and the frequency thereof is defined as frequency fP(t). The inflection point of which the frequency is farther from frequency fP(t−1) is determined to represent the body movement component, and the frequency thereof is thus defined as frequency fT(t). (S1007) In this case $f_{none}$ is again set to zero ($f_{none}$=0) (S1010) because a pulse wave component is present.

The sampling point counter t is then incremented to detect the inflection point count and frequency at the next sampling time (S1012).

By thereafter repeating this loop from S1004 to S1012, the pulse wave component can be extracted and a time when the pulse wave component cannot be discretely identified can be determined.

Third Embodiment

A pulsimeter according to a third embodiment of the present invention is described next below. The schematic diagram for this third embodiment is also shown in FIG. 3, and is identical to that of the first embodiment above. It should be noted that the first and second embodiments above have been described with reference to methods for processing a signal containing local changes. The program executed by CPU 305 according to the third embodiment is described below in accordance with a method for extracting a pulse wave component when a periodic body movement signal is superposed on a periodic pulse wave signal.

A pulse wave signal measured while running as exemplary of exercise with regular periodic motion is shown in FIG. 11A. Time (seconds) is shown on the horizontal axis in FIG. 11A with 128 sampling points obtained at 0.125 second intervals over a 16 second detection period plotted. The pulse wave signal level obtained by A/D conversion of the pulse wave signal potential by A/D converter 303 is shown on the vertical axis.

The result of applying a wavelet transform to the signal shown in FIG. 11A using a Daubechies function as the wavelet basis function is shown in FIG. 11B. As in FIG. 11A, time (second) is shown on the horizontal axis while frequency (Hz) is shown on the vertical axis. Shading in the graph indicates the relative level of the wavelet coefficient after wavelet transform; shading darkens as the coefficient level rises. As the level rises, the frequency component population at that point also rises. As a result, the frequency distribution of the pulse wave signal at each sampling time can be determined, thereby enabling the frequency component of body movement superposed to the pulse wave component and pulse wave signal to be determined.

The result of a fast Fourier transform applied to the pulse wave signal in FIG. 11A is shown in FIG. 11C. Note that there are two line spectra, one representing a pulse wave component and one a body movement component, and it is not possible to discriminate which is the pulse wave component.

The result of pulse wave component extraction from the wavelet transform result shown in FIG. 11B is shown in FIG. 12. As in FIGS. 11A and 11B, time (seconds) is shown on the horizontal axis, and 128 samples were taken at 0.125 sec intervals. The inflection point of the frequency extracted at each time point from the wavelet transform result (FIG. 11B) is plotted on the vertical axis in FIG. 12. Note that there are consistently two inflection points, representing the pulse wave component and body movement component. The inflection point frequency having the higher wavelet coefficient is plotted as a solid dot in FIG. 12, and the inflection point frequency with the lower wavelet coefficient is plotted as a solid triangle.

It should be noted that a basis function parameter is determined appropriately for a pulse wave signal before wave conversion, thereby enabling efficient time-frequency conversion of the pulse wave signal. As a result, the value of the wavelet coefficient is higher for the pulse wave component than the body movement component. It therefore follows that the inflection points plotted as solid dots can be determined to represent a pulse wave component.

An exemplary process for extracting a pulse wave component as described above is described next below with reference to the flow chart in FIG. 13.

Referring to FIG. 3 and FIG. 13, CPU 305 a pulse wave signal is detected (S1301), A/D converted (S1302) by A/D converter 303, and then time-frequency analyzed (S1304) by means of CPU 305 in accordance with a program as described below. Note that in a preferred embodiment of the invention this time-frequency analysis process is a wavelet transform operation. Note, further, that a parameter of the wavelet transform basis function used for this time-frequency analysis is determined (S1303) based on the number of inflection points obtained by differentiation of the detected pulse wave signal.

A sampling point counter t is then initialized to t=1 (S1305); sampling time is obtained as the sampling interval times t. Based on the wavelet transform result, inflection points are extracted from the frequency distribution at each sampling time (S1306).

The number of inflection points at each sampling time is then counted (S1307). If there is only one inflection point, it is determined that the subject was in a state of rest and there is no superposed body movement component. As a result, it can be determined that only a pulse wave component is present. The frequency fp(t) of the inflection point at this time is therefore stored (S1308), i.e., fp(t) is detected as the current pulse rate.

If there are two or more inflection points detected (S1307), the inflection point frequency with the higher wavelet coefficient is defined as frequency fp(t), and the inflection point frequency with the lower wavelet coefficient is defined as frequency fT(t) (S1309).

Sampling point counter t is then incremented to detect the inflection point count and frequency at the next sampling time (S1310). By thereafter repeating this loop, the pulse wave component can be extracted.

The pulse wave signal only can be emphasized and detected by creating a basis function that reflects the pulse wave signal features. More specifically, by creating an appropriate basis function, qualitatively different pulse and body movement signals superposed in a single detection signal can be efficiently separated. One method of determining a parameter of a wavelet transform function enabling efficient separation of mixed pulse and body movement signals is described below.

FIG. 14A shows a pulse wave detected from a subject at rest with no movement. A wave representing the second differential of the wave in FIG. 14A is shown in FIG. 14B. Note that there are three inflection points in this case. Features of the pulse wave can be extracted by obtaining the second differential, and the inflection point count can be scaled as a parameter of the wavelet function. Basis functions of a wavelet transform can be broadly classified as non-orthogonal, orthogonal, or biorthogonal. Commonly used basis functions include a Gabor transform as exemplary of a non-orthogonal basis function, Daubechies, Symlets, and Meyer transforms as exemplary of orthogonal basis functions, and a spline transform as exemplary of a biorthogonal basis function. A function convenient for time-frequency analysis is selected. It is also possible to write a function appropriate to a pulse wave.

A Daubechies transform, an orthogonal basis function, is used below by way of example only. Using N as the number of inflection points and $\phi(x)$ as the basis function, $$\psi N(x) = \Sigma q_k \phi_N(2x-k)$$

where $\phi_N(x)$ is obtained as $$\phi N(x) = \Sigma p_k \phi_N(2x-k) \qquad [1]$$

where $p_k$ and $q_k$ are constants.

f(x) is graphed in FIG. 15A and FIG. 15B for N=3 and N=8, respectively. A wavelet transform was then applied using this basis function. In the third embodiment parameter N of this basis function is set to N=3, i.e., f(x) shown in FIG. 15B is used.

It should be noted that the preceding embodiments have been described using only a pulse wave sensor for separating the pulse wave component and body movement component, and identifying the pulse wave component to obtain the pulse rate. To further improve precision, however, the pulse wave component can be more efficiently isolated by using a separate pulse wave sensor and body movement sensor. A functional block diagram for a pulsimeter so comprised is shown in FIG. 16.

It is also possible in the preceding embodiments to use a Wigner-Ville distribution as the time-frequency analyzer means.

Various methods of wearing a pulsimeter according to the present invention are shown in FIG. 17A–17D. As shown in FIG. 17A, a pulse wave sensor can be comprised in a finger sack 1701; a pulse wave sensor 1702 can be worn on a belt 1703 (FIG. 17B); or a pulse wave sensor 1704 can be worn as part of a watch band (FIG. 17C). The invention shall not be limited to a specific method of wearing the pulse wave sensor, which must only be worn on a part of the body in a manner whereby the pulse can be easily extracted. FIG. 17D is a detailed view of the pulsimeter of FIG. 17B.

As described above, the pulse rate can be detected and displayed while a subject is exercising in a manner producing regular (periodic) or irregular body movements by providing a pulse wave component extraction means for extracting a pulse wave component based on the result of a time-frequency analysis of a pulse wave signal output by a pulse wave sensor worn on a part of the body while exercising.

In addition, a parameter of the basis function used for time-frequency analysis can be set to a value facilitating pulse wave component extraction by further providing a parameter changing means.

It is furthermore possible by means of the present invention to evaluate the pulse wave detection state of a pulse wave sensor worn on the body.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

What is claimed is:

1. A pulsimeter worn by a user comprising:
    a pulse wave detector, said pulse wave detector detects at least one of a pulse wave component and a body movement component and outputs a pulse wave signal;
    a time-frequency analyzer, said time-frequency analyzer time-frequency analyzes the pulse wave signal responsive to said pulse wave detector; and
    a pulse wave extractor, said pulse wave extractor extracts, independent of any body movement component produced by movement of the user, the pulse wave component responsive to said time-frequency analyzer.

2. The pulsimeter according to claim 1, wherein said time-frequency analyzer time-frequency analysis is in accordance with a parameter of a function, said pulsimeter further comprising a parameter changing means for changing the parameter of the function based on a pulse wave signal obtained from the pulse wave detector when the user is at rest and a movement component is absent.

3. A pulsimeter worn by a user comprising:
    a pulse wave detector, said pulse wave detector detects at least one of a pulse component and a body movement component and outputs a pulse wave signal;
    a time-frequency analyzer, said time-frequency analyzer time-frequency analyzes the pulse wave signal responsive to said pulse wave detector;
    a pulse wave extractor, said pulse wave extractor extracts the pulse wave component responsive to said time-frequency analyzer; and
    a detection state evaluator, said detection state evaluator evaluates a pulse wave detection state of said pulse wave detector based on the pulse wave component extracted by said pulse wave extractor.

4. The pulsimeter according to claim 1 or 3, wherein said time-frequency analyzer time-frequency analyzes in accordance with a wavelet transform.

5. The pulsimeter according to claim 1 or 3, wherein said time-frequency analyzer time-frequency analyzes in accordance with a Wigner-Ville distribution.

6. A method of measuring a pulse wave of a user comprising the steps of:
    (a) detecting at least one of a pulse wave component representing a pulse measurement of a user and a movement component indicative of any movement by the user;
    (b) time-frequency analyzing the at least one detected pulse wave component and movement component;
    (c) extracting the pulse wave component from step (b) independent of any of the movement component.

7. A method according to claim 6,
    wherein step (b) comprises the step of applying a wavelet transform;
    wherein step (c) comprises the steps of
        determining any inflection points;
        counting a number of inflection points; and
        wherein if there is only one inflection point only the pulse wave component is present, and
        wherein if there are at least two inflection points the movement component is superimposed on the pulse wave component.

8. A method according to claim 7, wherein one of the at least two inflection points has a frequency furthest away from a previous frequency point is the movement component and another one of the at least two inflection points has a frequency closest to the previous frequency point is the pulse wave component.

9. A method according to claim 7, wherein the wavelet transform is a Symlets function.

10. A method according to claim 7, wherein the wavelet transform is a Daubechies function.

11. A method according to claim 6,
    wherein step (b) comprises the step of applying a wavelet transform;
    wherein step (c) comprises the steps of
        determining any inflection points;
        counting a number of inflection points; and
        wherein if there is only one inflection point only the pulse wave component is present, and wherein if there an absence of an inflection point the pulse wave component and the movement component are absent.

12. A method according to claim 11,
wherein if one inflection point is present and a frequency of the one inflection point is within a predetermined amount of a previous frequency then the one inflection point is a pulse wave component, if the one inflection point is present and the frequency of the one inflection point is without the predetermined amount of the previous frequency then the one inflection point is a movement component,
wherein if there are at least two inflection points then the pulse wave component and the movement component are present,
wherein one of the at least two inflection points has a frequency furthest away from a previous frequency point is the movement component and another one of the at least two inflection points has a frequency closest to the previous frequency point is the pulse wave component.

13. A method according to claim 6,
wherein step (b) comprises the step of applying a wavelet transform having a basis function parameter;
wherein step (a) further comprises the step of setting the basis function prior to step (b);
wherein step (c) comprises the steps of
determining any inflection points; and
counting a number of inflection points;
wherein if there is only one inflection point only the pulse wave component is present, and
wherein if there an absence of an inflection point the pulse wave component and the movement component are absent.

14. A pulsimeter worn by a user comprising:
(a) detecting means for detecting at least one of a pulse wave component representing a pulse measurement of a user and a movement component indicative of any movement by the user;
(b) time-frequency analyzing means for time-frequency analyzing the at least one detected pulse wave component and movement component sensed by said detecting means;
(c) extracting means for extracting the pulse wave component from said time-frequency analyzing means independent of any of the movement component.

15. A pulsimeter according to claim 14,
wherein said time-frequency analyzing means for further applying a wavelet transform;
wherein said extracting means for further
determining any inflection points;
counting a number of inflection points; and
wherein if there is only one inflection point only the pulse wave component is present, and
wherein if there are at least two inflection points the movement component is superimposed on the pulse wave component.

16. A pulsimeter according to claim 15, wherein one of the at least two inflection points has a frequency furthest away from a previous frequency point is the movement component and another one of the at least two inflection points has a frequency closest to the previous frequency point is the pulse wave component.

17. A pulsimeter according to claim 15, wherein the wavelet transform is a Symlets function.

18. A pulsimeter according to claim 15, wherein the wavelet transform is a Daubechies function.

19. A pulsimeter according to claim 14,
wherein said time-frequency analyzing means for further applying a wavelet transform;
wherein said extracting means for further
determining any inflection points;
counting a number of inflection points; and
wherein if there is only one inflection point only the pulse wave component is present, and
wherein if there an absence of an inflection point the pulse wave component and the movement component are absent.

20. A pulsimeter according to claim 19,
wherein if one inflection point is present and a frequency of the one inflection point is within a predetermined amount of a previous frequency then the one inflection point is a pulse wave component, if the one inflection point is present and the frequency of the one inflection point is without the predetermined amount of the previous frequency then the one inflection point is a movement component,
wherein if there are at least two inflection points then the pulse wave component and the movement component are present,
wherein one of the at least two inflection points has a frequency furthest away from a previous frequency point is the movement component and another one of the at least two inflection points has a frequency closest to the previous frequency point is the pulse wave component.

21. A pulsimeter according to claim 14,
wherein said time-frequency analyzing means for further applying a wavelet transform having a basis function parameter;
wherein said pulsimeter comprises a parameter changing means for setting the basis function;
wherein said extracting means for further
determining any inflection points;
counting a number of inflection points; and
wherein if there is only one inflection point only the pulse wave component is present, and
wherein if there an absence of an inflection point the pulse wave component and the movement component are absent.

* * * * *